(12) United States Patent
Monsigny et al.

(10) Patent No.: US 11,820,869 B2
(45) Date of Patent: Nov. 21, 2023

(54) METHOD FOR DEPOLYMERISING OXYGENATED POLYMER MATERIALS BY NUCLEOPHILIC CATALYSIS

(71) Applicant: Commissariat a l'Energie Atomique et aux Energies Alternatives, Paris (FR)

(72) Inventors: Louis Monsigny, Bures sur Yvette (FR); Thibault Cantat, Issy les Moulineaux (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 326 days.

(21) Appl. No.: 17/269,445

(22) PCT Filed: Aug. 13, 2019

(86) PCT No.: PCT/EP2019/071711
§ 371 (c)(1),
(2) Date: Feb. 18, 2021

(87) PCT Pub. No.: WO2020/038775
PCT Pub. Date: Feb. 27, 2020

(65) Prior Publication Data
US 2021/0238380 A1 Aug. 5, 2021

(30) Foreign Application Priority Data

Aug. 23, 2018 (FR) ...................................... 1857614

(51) Int. Cl.
*C08J 11/18* (2006.01)
(52) U.S. Cl.
CPC ............ *C08J 11/18* (2013.01); *C08J 2367/02* (2013.01); *C08J 2367/04* (2013.01); *C08J 2369/00* (2013.01)

(58) Field of Classification Search
USPC .......................................................... 521/48
See application file for complete search history.

(56) References Cited

FOREIGN PATENT DOCUMENTS

WO 2016/098021 A1 6/2016

OTHER PUBLICATIONS

Krall et al., "Controlled hydrogenative depolymerization of polyesters and polycarbonates catalyzed by ruthenium(II) PNN pincer complexes," Chemical Communications, 50: 4884-4887 (2014).
Nunes et al., "PET depolymerisation in supercritical ethanol catalysed by [Bmim]BF4]," Royal Society of Chemistry, 4: 20308-20316 (2014).
International Search Report issued in corresponding International Patent Application No. PCT/EP2019/071711 dated Sep. 18, 2019.

*Primary Examiner* — Terressa Boykin
(74) *Attorney, Agent, or Firm* — Morgan, Lewis & Bockius LLP

(57) ABSTRACT

The present invention relates to a method for depolymerising oxygenated polymer materials, in particular by nucleophilic catalysis and to the use of said method in the recycling of plastic materials and the preparation of aromatic and aliphatic compounds that can be used as fuel, synthesis intermediates, raw materials in the construction sector, and in the petrochemical, electrical, electronic, textile, aeronautical, pharmaceutical, cosmetic and agrochemical industry. The present invention also relates to a method for manufacturing fuels, electronic components, plastic polymers, rubber, medicines, vitamins, cosmetics, perfumes, food products, synthetic yarns and fibres, synthetic leathers, glues, pesticides, fertilisers comprising (i) a step of depolymerisation of oxygenated polymer materials according to the method of the invention and optionally (ii) a step of hydrolysis, and optionally (iii) a step of functionalisation and/or defunctionalisation.

16 Claims, 3 Drawing Sheets

METHOD FOR DEPOLYMERISING OXYGENATED POLYMER MATERIALS BY NUCLEOPHILIC CATALYSIS

Figure 1:
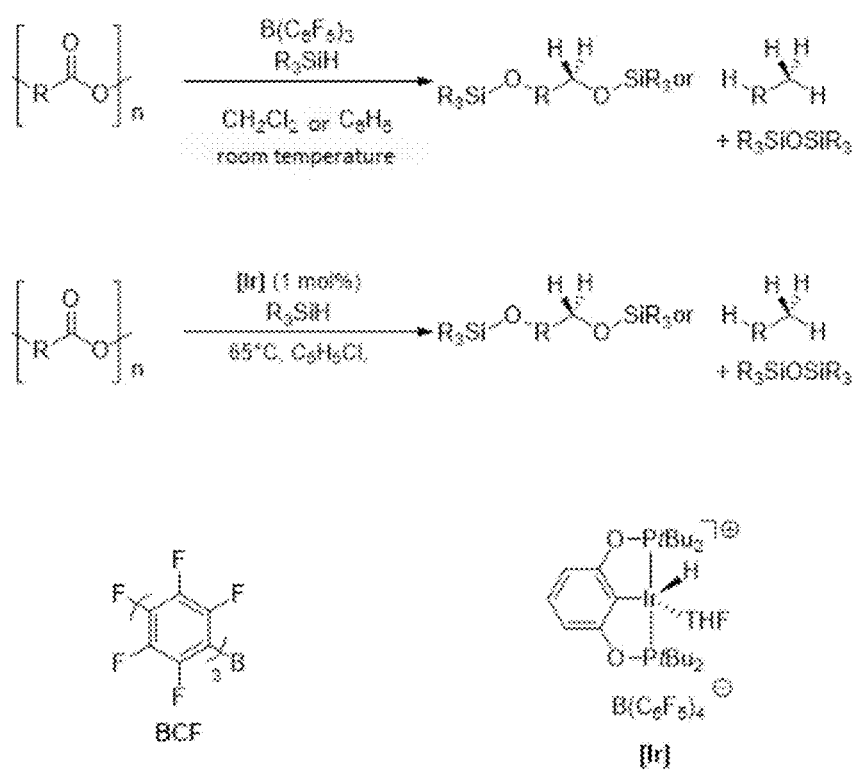

The present invention concerns a method for depolymerising oxygenated polymers, in particular by nucleophilic catalysis and the use of said method in recycling plastic materials and the preparation of aromatic and aliphatic compounds which can be used as fuel, synthesis intermediates, raw materials in the construction sectors, in the petrochemical, electric, electronics, textile, aeronautics, pharmaceutical, cosmetics, agrochemical industry.

The present invention also concerns a method for manufacturing fuels, electronic components, plastic polymers, rubber, medicaments, vitamins, cosmetic products, perfumes, food products, synthetic yarns and fibres, synthetic leathers, glues, pesticides, fertilisers comprising (i) a step of depolymerising oxygenated polymers according to the method of the invention and optionally (ii) a step of hydrolysis, and optionally (iii) a step of functionalisation and/or defunctionalisation.

Oxygenated polymers are currently base components of a large part of everyday materials and in particular, plastics. Indeed, a plastic material is mainly constituted of a polymer which after moulding and shaping operations, leads to obtaining a finished or semi-finished object. These plastics generally have high molecular masses and often come from petrochemistry, but there are plastics of natural origin. Nowadays, an increasing interest towards plastic materials is observed due to their ease of manufacture, of their relatively low cost, as well as the versatility that they present. However, the relative high cost of recycling these materials by using current methods poses economic problems requiring new solutions which could be agreed with the development of legislations. Thus, recycling materials containing oxygenated polymers has become a significant challenge of contemporary society.

Several recycling methods have been developed to cope with this problem. Among these methods, chemical recycling (or tertiary recycling) is a recycling method which is in accordance with the principles of sustainable development. Indeed, this type of recycling allows to recover components from petrochemistry, polymer material waste and plastic waste and use them as precursors in creating products with high added values. Polymer materials can thus be considered as a source of carbonaceous material (S. M. Al-Salem, P. Lettieri, J. Baeyens, *Progress in Energy and Combustion Science*, 2010, 36 (2010) pages 103-129; S. H. Park and S. H. Kim, *Fashion and Textiles*, 2014, 1, pages 1-17).

Chemical recycling methods are generally divided into two categories: those which regenerate starting monomers or oligomers (hydrolysis reactions) and those which generate other types of molecules having fine chemistry applications or as fuel (transesterification, aminolysis, methanolysis, glycolysis reactions, etc.). Numerous chemical recycling methods exist in the literature (D. S. Achilias, D. A. Louka, G. Tsintzou, I. A. Koutsidis, I. Tsagkalias, L. Andriotis, N. P. Nianias, P. Siafaka, *Recent Advances in the Chemical Recycling of Polymers (PP, PS, LDPE, HDPE, PVC, PC, Nylon, PMMA)*; INTECH Open Access Publisher, 2012, ISBN: 953510327X, 9789535103271; Chemically recyclable polymers: a circular economy approach to sustainability, Miao Hong and Eugene Y.-X. Chen, Green Chem., 2017, 19, 3692), etc.

Recently, two methods of choice have been developed: the reduction of oxygenated compounds with molecular hydrogen and hydrosilanes.

A) Hydrogenation

Hydrogenation is a method initially developed by Robertson et al. (*Chem. Commun.*, 2014, 50, 4884-4887) which allows the recycling of several types of polymers like polyesters and polycarbonates. This method uses a silane PNN ruthenium complex at 1% mol.

Reactions are made in the presence of anisole as a co-solvent in order to increase the solubility of polymers, and at a temperature of 160° C. and a pressure of 54.4 atm of H$_2$. PLA and PET, as well as a few polycarbonates (PC-BPA was not tested) have been depolymerised to provide for the first time diols with conversions going from 91 to >99% after 48 hours of reaction. Recently, Klankermayer et al. have developed a ruthenium-based catalyst, Ru(triphos)TMM, and triflimidic acid as co-catalyst (S. Westhues, J. Idel, J. Klankermayer, Molecular catalyst systems as key enablers for tailored polyesters and polycarbonate recycling concepts. *Sci. Adv.*, 2018, 4, eaat9669). This new systems achieves the reduction of polyesters and polycarbonates at 100 bar of hydrogen and 120° C. and requires a quantity of 0.1 to 1 mol % of catalyst Ru(triphos)TMM and triflimidic acid. Like the Robertson system, the Klankermayer system allows to recover diols from PET, PLA, but also PC-BPA with isolated yields going from 73 to 93%. These systems tolerate impurities and additives present in PET and PLA bottles. However, it presents the following disadvantages:

1. Depolymerisation reactions are carried out at high temperatures and pressures (i.e. temperatures >100° C. and pressures between 10 and 100 bars).
2. The reactions require the addition of additives like anisole (as co-solvent) and tBuOK (sensitive to air) or also triflimidic acid to activate the catalysts which catalysts will promote the hydrogenation reaction. The addition of these additives generally coming from a non-renewable source involves the use of a large quantity of starting carbon reagents which will require, subsequently, an additional recycling step to recover them.
3. The use of complexes containing a noble metal (ruthenium) and which are not commercial. Indeed, the synthesis of the complexes must be done in several steps and requires a sophisticated material with a high cost.

B) Hydrosilylation (by Electrophilic Activation of Hydrosilane)

This method has been recently developed by the Cantat group (*Chem Sus Chem*, 2015, 8, 980-984; WO2016/098021, *ACS Sustainable Chem. Eng.*, 2018, 6, 10481-10488) allowing the recycling of polyethers, polyesters and polycarbonates. This method calls upon a Lewis acid-type catalyst. The reaction is made according to a mechanism for the electrophilic activation of hydrosilane; a cationic silylated intermediary is generated using a Lewis acid promoter to achieve the depolymerisation of plastics such as PLA, PET and PC-BPA in silylated ethers or in alkanes with conversions going from 30 to 99% as shown in FIG. 1. This reaction is based fully on the use of the promoter (ideally a catalyst) of Lewis acid type. This system tolerates the impurities and the additives present in PET bottles. In addition to ester and carbonate bonds, this system has shown to be effective in the cleavage of ether bonds. However, improvements can be applied to it, in particular to improve the selectivity of the system, in particular regarding the selective cleavage of certain bonds of the oxygenated polymer. For example, if the oxygenated polymer contains ester bonds and ether bonds like polydioxanone (PDO), selectively cleaving the ester bonds by leaving the ether bonds intact, resort to solvents which are less dangerous for humans and for the environment, carry out the implementation of the depolymerisation of oxygenated plastics under more interesting conditions from the industrial point of view, like for example, the use of catalysts at least as effective, but less expensive and less sensitive to air and/or to water.

Figure 2:
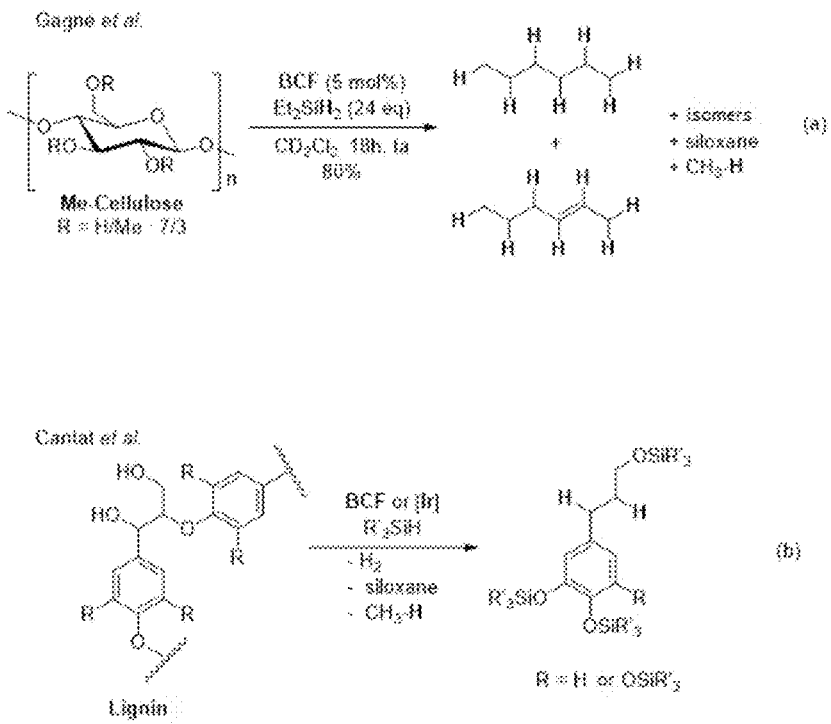

Lewis acids have shown their effectiveness in reducing biopolymers which are very difficult to depolymerise like for example methylcellulose (Gagné et al. Metal-Free Deoxygenation of Carbohydrates; *Angew. Chem. Int. Ed.* 2014, 53, 1646-1649 Gagné et al. (Metal-Free Deoxygenation of Carbohydrates; *Angew. Chem. Int. Ed.* 2014, 53, 1646-1649) or lignin (Feghali et al. *Energy Environ. Sci.*, 2015, 8, 2734-2743 and Monsigny et al., *Green Chem.*, 2018, 20, 1981-1986). In these systems, cleavage occurs at the level of the sp3—oxygen carbon bonds (ethers and alcohols) as shown in FIG. 2.

C) Hydrosilylation (by Nucleophilic Activation of Hydrosilane)

The chemical reactivity, as well as Lewis base-type catalyst applications (metal alkoxide and/or fluoride source, etc.) in hydrosilylation have been examined in detail in the literature (K. Revunova and G. I. Nikonov, Dalton Trans., 2014, DOI: 10.1039/C4DT02024C).

In particular, the hydrosilylation reaction by using this type of catalyst and/or initiator is very important in this sense that it opens new ways of synthesis to obtain new compounds by using mild conditions. In addition, the Lewis bases used are generally less expensive than catalysts allowing the electrophilic activation of hydrosilanes (Angew. Chem. Int. Ed. 2015, 54, 6931-6934). The hydrosilylation reaction catalysed by cesium fluoride CsF has initially been studied by Volpin et al., by Corriu et al. and by Hiyama et al. (M. Deneux, I. C. Akhrem, D. V. Avetissian, E. I. Mysoff and M. E. Volpin, Bull. Soc. Chim. France, (1973) 2638; Boyer, J.; Corriu, R. J. P.; Perz, R.; Reye, C. *J. Organomet. Chem.* 1979, 172, 143; Corriu, R. J. P.; Perz, R.; Reye, C. *Tetrahedron* 1983, 39, 999; M. Fujita and T. Hiyama, *J. Am. Chem. Soc.*, 106 (1984) 4629). This reaction has directly generated a considerable interest of several research groups throughout the world. The use of nucleophile as a catalyst in the hydrosilylation reaction has allowed the reduction of a great variety of organic substrates like aldehydes, imines and carboxylic acids, esters and amides. However, the reaction has never been developed on carbonates due to the low reactivity of this type of chemical functions and, consequently, their difficulty to be reduced. (Dub, P. A.; Ikariya, T. Catalytic Reductive Transformations of Carboxylic and Carbonic Acid Derivatives Using Molecular Hydrogen. ACS Catal. 2012, 2 (8), 1718-1741).

Moreover, although the hydrosilylation reaction by nucleophilic activation presents advantages, it has never been used in a depolymerisation reaction. This can be explained in several ways:

The reaction has been developed initially for synthetic chemistry applications and did not aim for enhancement in the field of materials which are often insoluble in conventional molecular chemistry solvents.

Hydrosilanes conventionally used in reductions, in particular those which are not by-products of the silicone industry, are expensive.

Polymeric materials and plastic waste in particular, contain a large quantity of contaminants and/or additives (such as pigments, etc.), which can deactivate most catalysts.

The operating conditions developed on small molecules or model molecules, are not necessarily transposable to polymers comprising the same functionalities. Indeed, while the small molecules are often soluble in conventional organic chemistry solvents, the corresponding polymers are not necessarily so, which can significantly alter the reactivity of these polymers.

Figure 3:
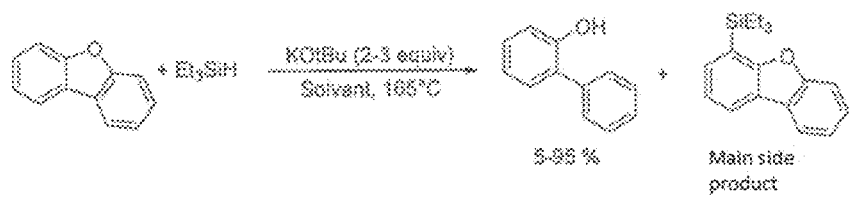

It must however be highlighted that Grubbs et al. (*Chem. Sci.*, 2013, 4, 1640-1645) have studied the use of potassium tert butanolate (KOtBu) stoichiometrically and non-catalytically (2-3 equivalents) in the presence of triethylsilane (Et$_3$SiH) for the reduction of aryl ether bonds in lignin model molecules, i.e. of oxygen carbon bond between two aromatics in a molecules mimicking a bond presents in a lignin polymer (FIG. 3). This reaction has led to a complex mixture of products and, more specifically, to a silylation reaction of aromatic carbons (called C-silylation) via a radical mechanism.

However, tertiary recycling methods present non-negligeable operational disadvantages like conducting the reaction at high temperature and at high pressures, as well as the use of metals and/or compounds which are expensive to catalyse the reactions. In addition, rare are the methods which allow to recycle at the same time several types of polymers (recycling of copolymers or mixture of polymers) and which resist additives and/or impurities present in the polymers.

Thus, there is a real need to develop an alternative method to the already-existing tertiary recycling methods of polymers, in particular oxygenated polymers, into compounds having a high added value overcoming the disadvantages of the tertiary recycling methods of the prior art.

In particular, there is therefore a real need to develop a depolymerisation method which could be applied to recycling polymers, in particular oxygenated polymers, into compounds having a high added value.

More specifically, there is a real need for a method for depolymerisation of polymers, in particular oxygenated polymers:

which leads to the formation of less oxygenated compounds (presenting less oxygen in the raw formula of the compound or even less C—O bonds, or in other words, compounds having an atom ratio O/(C+H) lower than the starting compound;

respectful of the environment;

which could be implemented under mild operating conditions and industrially interesting;

avoiding the use of polluting and expensive metal-based catalysts;

which is effective, the effectiveness being conveyed by a good conversion (at least 50% mol. with respect to the number of monomer units of the starting polymer), and even a total conversion of the oxygenated polymer in chemical compounds, with a good purity (at least 90% mol. with respect to the total number of moles of compounds obtained) or which could be easily purified;

with a good selectivity with respect to the chemical compounds obtained;

allowing a selective cleavage of certain bonds of the oxygenated polymer;

which is general and versatile which can be adapted to the oxygenated polymer to be depolymerised; and/or capable of resisting to additives and/or impurities (or contaminants) possibly present in oxygenated polymers to be depolymerised.

The present invention has precisely for aim to respond to these needs by providing a method for depolymerising oxygenated polymers by selective cleavage of oxygen-carbon bonds of ester functions (—CO—O—) and carbonate functions (—O—CO—O—), characterised in that it comprises a step of putting said oxygenated polymers into contact with a hydrosilane compound of formula (I)

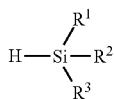
(I)

wherein
$R^1$, $R^2$ and $R^3$ represent, independently from one another, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino group being optionally substituted, or $R^1$ is such as defined above and $R^2$ and $R^3$, taken together with the silicon atom to which they are bonded form a silylated heterocycle optionally substituted;

in the presence of a Lewis base type catalyst.

More specifically, the object of the invention is a method for depolymerising oxygenated polymers by selective cleavage of oxygen-carbon bonds of ester functions (—CO—O—) and carbonate functions (—O—CO—O—), characterised in that it comprises a step of putting said oxygenated polymers into contact with a hydrosilane compound of formula (I)

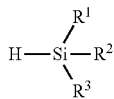
(I)

wherein
$R^1$, $R^2$ and $R^3$ represent, independently from one another, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted, or $R^1$ is such as defined above and $R^2$ and $R^3$, taken together with the silicon atom to which they are bonded form a silylated heterocycle optionally substituted;

in the presence of a Lewis base type catalyst, said Lewis base type catalyst being
an alcoholate of formula (II)

$$(R^6-O^-)_w M^{w+} \qquad (II)$$

wherein
w is 1, 2, 3, 4, and 5;
$R^6$ is an alkyl comprising 1 to 6 carbon atoms, an alkenyl comprising 2 to 6 carbon atoms, an alkynyl comprising 2 to 6 carbon atoms or a typically bi- or tri-cyclic monocyclic or polycyclic aryl comprising 6 to 20 carbon atoms; and M is a metal chosen from among Li, Na, K, Cs or Rb Cu, Mg, Zn, Ca, Sr, Ba, Pb, Al, Sb, La, Zr, Si, Ti, Sn, Hf, Ge, V; or a compound allowing to release a fluoride (F⁻) of formula (III):

$$Y^{z+}-(F^-)_z \qquad (III)$$

wherein
z is 1, 2, 3, 4;
Y is an alkyl ammonium of which the alkyl comprises 1 to 6 carbon atoms, an alkenyl ammonium of which the alkenyl comprises 2 to 6 carbon atoms, an alkynyl ammonium of which the alkynyl comprises 2 to 6 carbon atoms or an aryl comprising 6 to 10 carbon atoms; a quinine ammonium, or
Y is a metal chosen from among Li, Na, K, Cs, Rb, Cu, Zn, Ca, Ba, Al, Zr, Sn;

a fluorosilicate chosen from among:
hexafluorosilicates $SiF_6^{2-}$ with an alkaline counterion chosen from among Li, Na, K and Cs; or
fluorosilicates of formula $(R^7)_3 SiF_2^-$ with an alkyl ammonium counterion of formula $N(R^{10})_4^+$ or a sulfonium counterion of formula $S(R^{11})_3^+$; with
  $R^7$ being an alkyl comprising 1 to 6 carbon atoms chosen from among methyl, ethyl, propyl, butyl, pentyl or hexyl and their branched isomers; or an aryl comprising 6 to 10 carbon atoms chosen from among phenyl, benzyl or naphthyl;
  $R^{10}$ being a hydrogen atom; a methyl, an ethyl, a propyl, a butyl, and their branched isomers;
  $R^{11}$ being a hydrogen atom; a methyl, an ethyl, a propyl, a butyl, and their branched isomers or primary, secondary or tertiary amines;

a primary or secondary amide, a guanidine derivative chosen from among
sodium or potassium bicyclic guanidinates, in particular sodium or potassium salt of the anion of 1,3,4,6,7,8-hexahydro-2H-pyrimido[1,2-a]pyrimidine (or Hhpp),
guanidine,
1,5,7-triazabicyclo[4.4.0]dec-5-ene (or TBD);
a carbenic heterocycle of general formula (IV):

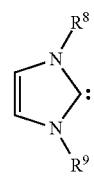
(IV)

wherein
$R^8$ and $R^9$ represent, independently from one another, an alkyl comprising 1 to 6 carbon atoms, an alkenyl comprising 2 to 6 carbon atoms, an alkynyl comprising 2 to 6 carbon atoms or a bi- or tri-cyclic aryl comprising 6 to 20 carbon atoms;

a carbonate of formula (V)

$$M'_2 CO_3 \qquad (V)$$

wherein M' is a metal chosen from among Li, Na, K, Cs or Rb.

In the sense of the invention, an oxygenated polymer is a polymer comprising at least one oxygenated polymer and possibly at least one additive and/or one impurity (or contaminant).

In the context of the present invention, an oxygenated polymer means a polymer or copolymer of which the repeated units of the main chain contain the ester function (—CO—O—) also called polyesters or the carbonate function (—O—CO—O—) also called polycarbonates.

The oxygenated polymers of the invention are mainly synthetic or semi-synthetic polymers, but can also be natural and biosourced polymers, i.e. coming from the animal or plant biomass. The additive(s) optionally present in the material can be introduced before or during the shaping of the material, to apply or improve one (or sometimes more) specific property(ies). As an example of additives, stabilisers, antioxidants, colourants, pigments, wetting agents, dispersants, emulsifiers, thickeners, biocides, plasticisers, photoprotectors, etc. can be mentioned.

In the context of the present invention, the terms "impurities" and "contaminants" mean compounds having been in contact with the polymer according to its origin and its use (for example, proteins in the case of a milk bottle, the sugar in soda bottles, the glue used to glue labels onto bottles, etc.). In this description, the terms "impurities" and "contaminants" can equally be used.

The method of the invention has the advantage of resisting to the presence of additive(s) and/or impurities (or contaminants) in the polymers. No problem of catalyst intoxication has been observed with additives commonly used in the polymers. Indeed, the biggest challenge of recycling is not limited to the depolymerisation of the polymer present alone in the reaction medium (pure polymer), but also extends to its depolymerisation in a commercial material which could contain additives like colourants, mineral fillers, antioxidants, etc. The presence of these additives in the material can deactivate the catalyst used to achieve the depolymerisation, and thus make the reaction ineffective. The method of the invention therefore presents a great industrial interest, as it is capable of resisting to the additives and/or impurities (or contaminants) present in the starting polymer, which, for example, can be plastic waste.

The Lewis bases used in this invention as catalyst have the advantage of being generally less expensive than the Lewis acids and can be used in the absence of solvents or solvents which generally cause little harm, such as THF, methylTHF, anisole, PEG 400, etc.

The hydrosilylation reaction catalysed by Lewis bases is more selective than the hydrosilylation reaction catalysed by Lewis acids, since the $sp^3$-oxygen carbon bonds remain intact.

The depolymerisation method of the invention leads to the formation of one single product in the form of silyl ether, i.e. a chemical compound containing siloxy groups (—O—$SiR_1R_2R_3$). The hydrolysis of said silyl ether can occur in situ without intermediate treatment steps i.e without isolating the siloxy products.

The hydrosilanes used in this new method are cheap and produced on a large scale.

The starting oxygenated polymers can be an oxygenated polymer, or a mixture of oxygenated polymers, or a mixture of at least two polymers of which at least one is an oxygenated polymer in the sense of the invention, with optionally one or more additive(s) and/or an impurity (or contaminant).

According to an embodiment of the invention, the oxygenated materials of the invention comprise one or more additive(s).

When the oxygenated polymer is a copolymer, the main chain of said copolymer can comprise repeated units containing one or more ester functions (—CO—O—) and/or one or more carbonate functions (—O—CO—O—) and optionally repeated units chosen from among ethylenic, propylenic, vinylic units substituted by one or more chlorine or fluorine atoms, styrene, styrene-butadiene, acrylic, methacrylic.

In the following description, the term "polymer" can also mean a "copolymer". Thus, the term "polymer" can cover homopolymers (a polymer coming from one single monomer species) and copolymers (a polymer coming from at least two different monomers).

The synthetic or semi-synthetic oxygenated polymers of the invention can be chosen from among:
  saturated or unsaturated polyesters chosen, for example, from among polylactic acid (PLA), polycaprolactone (PCL), polyhydroxyalkanoate (PHA), polyhydroxyvalerate (PHV), polyethylene adipate (PEA), polybutylene succinate (PBS), poly(3-hydroxybutyrate-co-3-hydroxyvalérate (PHBV), polyethylene terephthalate (PET), polybutylene terephthalate (PBT), polytrimethylene terephthalate (PTT), polyethylene naphthalate (PEN), polydioxanone (PDO);
  polycarbonates chosen, for example, from among PC-BPA, polypropylene carbonate (PPC), polyethylene carbonate (PEC), poly(hexamethylene carbonate), allyl diglycol carbonate (ADC) or CR-39.

From among oxygenated polymers, polyethylene terephtalate (PET), polylactic acid (PLA) and polycarbonate (PC-BPA) are the most studied in the literature, as their recycling has several interests:
  Polyethylene terephthalate (PET) is one of the most commonly used plastics in the world due to its lightness, its durability and its chemical resistance, but also its low cost.
  Polylactic acid (PLA) is very interesting from an environmental point of view, since it is mainly derived from renewable resources, such as maize, potatoes and other agricultural products. Due to its biodegradability combined with its mechanical resistance and its transparency, PLA is considered as a green and durable material which can be seen as a promising alternative to petroleum-based polymer resins, in particular PET.
  Polycarbonates (PC-BPA) are thermoplastics having excellent mechanical properties and a large resistance to impacts, a UV resistance, as well as an excellent electrical resistance. Consequently, polycarbonates are used in a great variety of applications like compact discs, armoured windows, food packaging or fizzy drinks bottles.

In the context of the invention, oxygenated polymers can also be biosourced and be, more specifically, coming from the plant biomass of which the aromatic units are bonded by ester bonds. In this regard, water-soluble tannins can be mentioned, in particular gallotannins and ellagitannins, and suberin.

Oxygenated polymers are advantageously chosen from among
  polyesters chosen from among PET, PCL, PDO or PLA;
  polycarbonates chosen from among PC-BPA or PPC;
  water-soluble tannins chosen from among gallotannins, ellagitannins, or suberin.

As already indicated, the materials of the invention can be a mixture of at least two polymers, of which at least one is an oxygenated polymer in the sense of the invention. In this case, the other polymer(s) present in the material can be chosen from among polyolefins, in particular polyethylene and polypropylene; polyvinyl acetate (PVAC), polyvinyl alcohol (PVAL); polystyrene (PS), acrylonitrile butadiene styrene (ABS); styrene-butadiene (SBR); acrylonitrile styrene acrylate (ASA); saturated or crosslinked polyurethanes; methyl polymethacrylate (PMMA), polyacrylonitrile (PAN); polyvinyl chloride (PVC), polyvinylidene chloride (PVDC); polytetrafluoroethylene (PTFE), polyvinyl fluoride (PVF), polyvinylidene fluoride (PVDF), ethylene tetrafluoroethylene (ETFE), perfluoroalkoxy (PFA); polyetheretherketone (PEEK); styrene-butadiene-styrene sequenced copolymers (SBS); polyamides like PA6, PA 12, PA 6.6; polyurethanes; polyureas; polyurea and polyurethane copolymers (known under the names of Spandex, Lycra or elastane).

By carefully controlling the operating conditions, the depolymerisation of a polymer comprising a mixture of polyester(s) and/or polycarbonate(s) can be selective. For example, in the case of a mixture PPC+PLA, the PLA is cleaved first. In the case of a mixture of PC-BPA+PLA, it is the PC-BPA which is cleaved first due to electronic effects. In the case of a PET+PLA mixture, the PET is cleaved first due to electronic effects. The depolymerisation method according to the invention can generally lead to the formation of chemical compounds in the liquid state liked glycol ethylene and/or to the solid state like bisphenol A (BPA).

Whatever the nature of the starting polymer used, the nature of the hydrosilane and its quantity, the catalyst used and the duration of the reaction, the nature of the depolymerisation product remains unchanged. Thus, the products obtained are always silyl ethers which can be hydrolysed to provide the corresponding diols.

Indeed, one of the advantages of the method of the invention is the great selectivity towards one single type of product obtained from one same polymer. For example, in the case of PET, the depolymerisation method only leads to the obtaining of 1,4-phenylene dimethanol and ethylene glycol. No other product is observed in the depolymerisation of the PET.

In the context of the present invention, the selectivity concerns the nature of the products formed, as well as the nature of the cleaved bonds.

The bonds selectively targeted and cleaved by the depolymerisation method of the invention are oxygen-carbon bonds of carbonyl type of the ester functions (—CO—O—) and carbonate functions (—O—CO—O). Thus, the C—O bonds of the functionalities wherein the carbon atom is bonded to another carbon atom by one single carbon $sp^3$—oxygen bond, a multiple $sp$ or $sp^2$ bond (for example, C═C—O) are not cleaved during the depolymerisation method of the invention. For example, the alkyl ethers present in polyethylene glycol (PEG) or even aryl ethers present in polyphenols, are not cleaved. Single, double and triple C—C bonds are not cleaved either by the depolymerisation method of the invention. For example, polystyrene (PS) is not depolymerised by the method of the invention.

According to the operating conditions, during the depolymerisation method, the carbonyl function —C═O is reduced into a silylated ether —CH—OSiR$^1$R$^2$R$^3$ where R$^1$, R$^2$, and R$^3$ are such as defined for the formula (I) in the context of the present invention.

The depolymerisation method of the invention is of great versatility, in particular with respect to the oxygenated starting polymer materials.

On the other hand, the depolymerisation step in the method of the invention can be carried out under mild operating conditions, i.e. mild temperatures (15° C. to 75° C.) and low pressures (1 to 5 bars, preferably 1 to 2 bars) and allows to avoid drastic reaction conditions of temperature and pressure used traditionally, for example, in the recycling of polymer materials.

In addition, the use of so-called "green" solvents is an asset for this system. Under certain conditions of the present invention, no solvent is used. This is an important advantage for respecting the environment.

The method for depolymerising oxygenated polymer materials according to the invention provides chemical compounds which could contain siloxy groups and having a number of carbons more reduced than that of the oxygenated polymer(s) present in the starting material. The compounds obtained can lead to, after hydrolysis reactions, to chemical compounds of average molar mass less than 600 g/mol.

Moreover, the yield of chemical compounds of average molar mass less than 600 g/mol obtained by the depolymerisation method and after the hydrolysis step, depends on the starting polymer material, as well as the operating conditions applied. The yield is generally good (68 to 98% mol. with respect to the total number of moles of monomer units present in the polymer(s) of the starting material). By approximation, and in order to calculate the molar yield of the depolymerisation method, the starting polymer material is considered to be exclusively formed from the polymer studied.

The yield is then calculated by applying the following formula:

$$\text{Yield} = n \text{ (target molecule)}/n \text{ (monomer units)} \times 100$$

with n (target molecule) being the number of moles of the molecule that is sought to be obtained after depolymerisation and having an average molar mass less than 600 g/mol obtained after hydrolysis, and n (monomer units) being the total number of moles of monomer units present in the starting polymers.

The purity of the molecules obtained after depolymerisation can be calculated as follows:

$$\text{Purity} = n \text{ (target molecule)}/n \text{ (molecules obtained coming from the polymer)} \times 100$$

with n (target molecule) being the number of moles of the molecule that is sought to be obtained after depolymerisation and having an average molar mass less than 600 g/mol obtained after hydrolysis, and n (molecules obtained coming from the polymer) being the number of moles of all the molecules derived from the monomer units of the polymer, including the by-products, obtained after the depolymerisation reaction.

The conversion of the starting oxygenated polymer after depolymerisation can be calculated as follows:

$$\text{Conversion} = n \text{ (molecules obtained)}/n \text{ (monomer units)} \times 100$$

with n (molecules obtained) and n (monomer units) such as defined above.

The depolymerisation of natural oxygenated biosourced, synthetic or semisynthetic polymers can generate mono-, bi- and/or tri-cyclic and mono- or polyoxygenated, for example di- and/or tri-oxygenated aromatic molecules. For example, in the case of the depolymerisation of natural oxygenated polymers, the depolymerisation products can be monocyclic aromatic compounds (case of gallotannin, for example), mono- bi- and/or tri-cyclic (case of ellagitannin, for example) and possibly mono-, di-, and/or tri-oxygenated.

The depolymerisation of natural, biosourced, synthetic or semisynthetic oxygenated polymers can also generate non-aromatic (or aliphatic) saturated or unsaturated molecules, presenting ether (or not) bonds, constituted of carbon and hydrogen atoms which could be mono-, di-, and/or tri-oxygenated.

By "alkyl", it is meant, in the sense of the present invention, a linear, branched or cyclic, saturated, optionally substituted carbon radical, comprising 1 to 12 carbon atoms, preferably 1 to 8 carbon atoms, for example 1 to 6 carbon atoms. As a saturated, linear or branched alkyl, for example methyl, ethyl, propyl, butyl, pentyl, hexyl, octyl, nonyl, decyl, undecyl, dodecanyl radicals and their branched isomers can be mentioned. As cyclic alkyl, cyclopropyl, cyclobutyl, cyclopentyl, cyclohexyl, bicyclo[2,1,1] hexyl, bicyclo[2,2,1] heptyl radicals can be mentioned. As cyclic alkyls carrying an unsaturation, for example, cyclopentenyl, cyclohexenyl can be mentioned.

By "alkenyl" or "alkynyl", it is meant an unsaturated linear, branched or cyclic, optionally substituted carbon radical, said unsaturated carbon radical comprising 2 to 12 carbon atoms, preferably 2 to 8 carbon atoms, for example 2 to 6 carbon atoms, comprising at least one double bond (alkenyl) or a triple bond (alkynyl). In this regard, for example, ethylenyl, propylenyl, butenyl, pentenyl, hexenyl, acetylenyl, propynyl, butynyl, pentynyl, hexynyl radicals and their branched isomers can be mentioned.

When in the alkyl, alkenyl and alkynyl radicals such as defined above, at least 1 $sp^3$ carbon atom, is replaced by at least one heteroatom chosen from among nitrogen, oxygen, boron, silicon, phosphorus or sulphur, this is a "heteroalkyl", "heteroalkenyl" and "heteroalkynyl" radical, respectively. As an indication, methoxyl, ethoxyl, butoxyl, pentoxyl, thiomethoxyl, dimethylaminyl and their branched isomers can be mentioned.

Alkyl, heteroalkyl, alkenyl, heteroalkenyl, alkynyl, and heletoalkynyl groups in the sense of the invention, can be optionally substituted by one or more hydroxyl groups; one or more alkoxy groups; one or more siloxy groups; one or more halogen atoms chosen from among fluorine, chlorine, bromine and iodine atoms; one or more nitro (—$NO_2$) groups; one or more nitrile (—CN) groups; one or more aryl groups; with the alkoxy, siloxy and aryl groups such as defined in the context of the present invention.

The term "aryl" generally means a cyclic aromatic substituent comprising 6 to 20, preferably 6 to 12 carbon atoms, for example 6 to 10 carbon atoms. In the context of the invention, the aryl group can be mono- or polycyclic. As an indication, phenyl, benzyl and naphthyl groups can be mentioned. The aryl group can be optionally substituted by one or more hydroxyl groups, one or more alkoxy groups, one or more siloxy groups, one or more halogen atoms chosen from among fluorine, chlorine, bromine and iodine atoms, one or more nitro (—$NO_2$) groups, one or more nitrile (—CN) groups, one or more alkyl groups, with alkoxy, siloxy and alkyl groups such as defined in the context of the present invention.

The term "heteroaryl" generally means a mono- or polycyclic aromatic substituent comprising 5 to 10 members, preferably 5 to 7 members, of which at least 2 carbon atoms, and at least one heteroatom, chosen from among nitrogen, oxygen, boron, silicon, phosphorus and sulphur. The heteroaryl group can be mono- or polycyclic. As an indication, furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidilyl, pyrazinyl, triazinyl, cinnolinyl, phtalazinyl, quinazolinyl groups can be mentioned. The heteroaryl group can be optionally substituted by one or more hydroxyl groups, one or more alkoxy groups, one or more halogen atoms chosen from among fluorine, chlorine, bromine and iodine atoms, one or more nitro (—$NO_2$) groups, one or more nitrile (—CN) groups, one or more aryl groups, one or more alkyl groups, with alkyl, alkoxy and aryl groups such as defined in the context of the present invention.

The term "alkoxy" means an alkyl, alkenyl and alkynyl group, such as defined above, bonded by an oxygen atom (—O-alkyl, O-alkenyl, O-alkynyl).

The term "aryloxy" means an aryl group such as defined above, bonded by an oxygen atom (—O-aryl).

The term "heterocycle" generally means a mono- or polycyclic substituent, comprising saturated or unsaturated 5 to 10 members, preferably 5 to 7 members, containing 1 to 4 heteroatoms chosen independently from one another, from among nitrogen, oxygen, boron, silicon, phosphorus and sulphur. As an indication, morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl, isothiazolidinyl substituents can be mentioned. The heterocycle can be optionally substituted by one or more hydroxyl groups, one or more alkoxy groups, one or more aryl groups, one or more halogen atoms, chosen from among fluorine, chlorine, bromine and iodine atoms, one or more nitro (—$NO_2$) groups, one or more nitrile (—CN) groups, one or more alkyl groups, with alkyl, alkoxy and aryl groups, such as defined in the context of the present invention.

By halogen atom, it is meant an atom chosen from among fluorine, chlorine, bromine and iodine atoms.

By "silyl" or "silylated" group, which can be used interchangeably, it is meant a group of formula [—Si(X)$_3$], wherein each X, independently from one another, is chosen from among a hydrogen atom; one or more halogen atoms chosen from among fluorine, chlorine, bromine or iodine atoms; one or more alkyl groups; one or more alkoxy groups; one or more aryl groups; one or more siloxy groups; one or more silyl groups; with alkyl, alkoxy, aryl and siloxy groups such as defined in the context of the present invention.

By "siloxy" group, it is meant a silylated group, such as defined above, bonded by an oxygen atom (—O—Si(X)$_3$) with X such as defined above. In the sense of the invention, by "silylated heterocycle", it is meant a mono- or polycyclic substituent, comprising saturated or unsaturated 5 to 15 members, preferably 5 to 7 members, containing at least one silicon atom and optionally at least one other heteroatom chosen from among nitrogen, oxygen and sulphur. Said silylated heterocycle can be optionally substituted by one or more hydroxyl groups; one or more alkyl groups, one or more alkoxy groups; one or more halogen atoms chosen from among fluorine, chlorine, bromine and iodine atoms; one or more aryl groups, with alkyl, alkoxy and aryl groups such as defined in the context of the present invention. From among the silylated heterocycles, for example, 1-silacyclo-3-pentene or 1-methyl-1-hydrido-1-silacyclopentadiene can be mentioned as represented below:

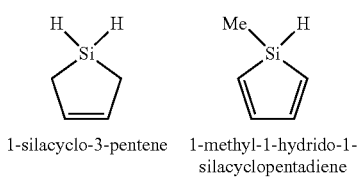

1-silacyclo-3-pentene    1-methyl-1-hydrido-1-silacyclopentadiene

From among silylated heterocycles, for example, methyl siloxane, 1-phenyle-1-silacyclohexane, 1-sila-bicyclo[2.2.1]heptane, 1-methyl-1-silacyclopentane, 9,9-dihydro-5-silafluorene responding to the following semi-developed formulas can also be mentioned:

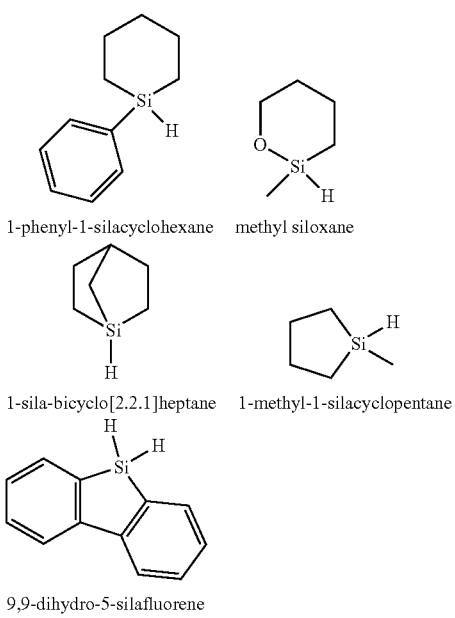

1-phenyl-1-silacyclohexane    methyl siloxane 1-sila-bicyclo[2.2.1]heptane    1-methyl-1-silacyclopentane 9,9-dihydro-5-silafluorene By polyol, it is meant an organic compound characterised by the presence of a certain number of hydroxyl (—OH) groups. In the context of this invention, a polyol compound contains at least two hydroxyl groups. More specifically, by "polyol" this means a compound of formula Y—(OH)$_m$, wherein m is greater than or equal to 1, and Y is chosen from among one or more alkyl groups, one or more alkoxy groups, one or more siloxy groups, one or more aryl groups, one or more heteroaryl groups with alkyl, alkoxy, siloxy, aryl and heteroaryl groups, such as defined in the context of the present invention.

By "amino" group, it is meant a group of formula —NR$^4$R$^5$, wherein:
R$^4$ and R$^5$ represent, independently from one another, a hydrogen atom, an alkyl group, an alkenyl group, an alkynyl group, an aryl group, a heteroaryl group, a heterocycle, a silylated group, a siloxy group, with alkyl, alkenyl, alkynyl, aryl, heteroaryl, heterocycle, silylated, and siloxy groups, such as defined in the context of the present invention; or
R$^4$ and R$^5$, taken together with the nitrogen atom to which they are bonded, form a heterocycle optionally substituted by one or more hydroxyl groups; one or more alkyl groups; one or more alkoxy groups; one or more halogen atoms chosen from among fluorine, chlorine, bromine and iodine atoms; one or more nitro (—NO$_2$) groups; one or more nitrile (—CN) groups; one or more aryl groups; with alkyl, alkoxy and aryl groups such as defined in the context of the present invention.

In the context of the invention, "suberin" means a biosourced polymer mainly found in higher plants. This waxy organic substance is impermeable and is found on the cellulosic walls of certain plant cells, in particular those of the cork of which it constitutes the main component. Suberin contains two domains: that of polyaliphatics and that of polyaromatics mainly formed of hydroxycinnamic acid derivatives. The precise composition of suberin varies according to the species.

The tannin means a biosourced polymer contained in numerous plants. This organic substance can be, for example, contained in leaves (sumac), barks and wood (e.g. oak, acacia) and/or roots (badan) of plants. This amorphous polyphenolic compound is particularly used in the tanning of skin to make leather, the manufacture of inks or in pharmacology. There are three main categories of tannins: water-soluble tannins, non-water-soluble or condensed tannins, and phlorotannins. This definition comprises pseudo-tannins which are tannins of low molecular weight bonded to other compounds.

By hydrolysable tannins, in the sense of the invention, it is meant compounds constituted of glucose polygalloyl mixtures (these are polymers of molecules formed from gallic acid derivatives and β-D-glucose, like for example, in the case of tannic acid) and/or polygalloyl derivatives of quinic acid containing between 3 and 12 gallic acid units per molecule. These compounds mainly contain ester bonds bonding aromatic units to a polyol, which facilitates its hydrolysis by weak acids or bases.

By gallotannins, it is meant hydrolysable tannins derived from gallic acid, wherein the gallic acid is bonded by ester bonds to a central polyol. In these compounds, the galloyl units can likewise undergo oxidative cross couplings (oxidative cross coupling in English) or esterification reactions. There are several types of gallotannins mainly distributed according to their chemical composition, like for example: glucose galloyls (these are molecules formed from a bond between gallic acid and β-D-glucose), the galloyls of quinic acids, galloyls of shikimic acids.

By "ellagitannin", in the sense of the invention, it is meant gallotannins or galloyl groups having undergone a C—C oxidative coupling. This intramolecular coupling is carried out for most plants between carbon atoms: C2 and C3 or between C4 and C6. This type of polyphenol generally forms macrocycles, while this is not observable with gallotannins.

By "catalyst", in the sense of the invention, it is meant any compound capable of modifying, in particular by increasing, the speed of the chemical reaction to which it contributes, and which is regenerated at the end of the reaction. This definition comprises both catalysts, i.e. the compounds which exercise their catalytic activity without needing to undergo any one modification or conversion, and the compounds (called also pre-catalysts) which are introduced in the reactional medium and which are converted there into a catalyst. In the method of the invention, the catalyst is a Lewis base.

It is in particular necessary that the catalyst is chosen by considering in particular its steric hindrance, its ability to activate the hydrosilane compound and its solubility in the reaction medium.

In the sense of the invention, a Lewis or nucleophilic base is a chemical entity of which one of the components has a pair or more of free non-binding electrons on its valence layer. They can form covalent bonds coordinated with a Lewis acid.

In the method of the invention, the Lewis base can be an alcoholate of formula (II), a compound allowing to release a fluoride of formula (III) or a fluorosilicate of formula (IV).

According to a particular embodiment of the invention, the Lewis base-type catalyst is an alcoholate of formula (II)

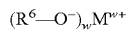  (II)

wherein
w is 1, 2, 3, 4, and 5;
$R^6$ is an alkyl comprising 1 to 6 carbon atoms, an alkenyl comprising 2 to 6 carbon atoms, an alkynyl comprising 2 to 6 carbon atoms or a monocyclic or polycyclic typically bi- or tri-cyclic aryl comprising 6 to 20 carbon atoms; and
M is a metal chosen from among Li, Na, K, Cs or Rb Cu, Mg, Zn, Ca, Sr, Ba, Pb, Al, Sb, La, Zr, Si, Ti, Sn, Hf, Ge, V.

In this embodiment, preferably $R^6$ is a linear or branched alkyl comprising 1 to 6 carbon atoms, chosen from among methyl, ethyl, propyl, butyl, pentyl or hexyl and their branched isomers.

In this embodiment, M is preferably Li, Na, K or Rb.

In the catalyst of formula (II), $R^6$ is a linear or branched alkyl comprising 1 to 6 carbon atoms, chosen from among methyl, ethyl, propyl, butyl, pentyl or hexyl and their branched isomers and M is Li, Na, K or Rb.

Still in this embodiment, the alcoholate is preferably chosen from among $CH_3$—OLi, $CH_3$—ONa, $CH_3$—OK, $CH_3$—ORb, $CH_3CH_2$—OK, $(CH_3$—$O)_3Al$, $(PhO)_3Al$, $(iPrO)_3Al$ or tBu-OK.

In this particular embodiment, the catalyst of formula (II), is preferably the alcoholate is tBu-OK.

According to another particular embodiment of the invention, the Lewis base-type catalyst is a compound allowing the release a fluoride of formula (III):

  (III)

wherein
z is 1, 2, 3, 4;
Y is an alkyl ammonium of which the alkyl comprises 1 to 6 carbon atoms, an alkenyl ammonium of which the alkenyl comprises 2 to 6 carbon atoms, an alkynyl ammonium of which the alkynyl comprises 2 to 6 carbon atoms or an aryl comprising 6 to 10 carbon atoms; a quinine ammonium, or
Y is a metal chosen from among Li, Na, K, Cs, Rb, Cu, Zn, Ca, Ba, Al, Zr, Sn.

In this embodiment, preferably Y is alkyl ammonium of which alkyl comprises 1 to 6 carbon atoms chosen from among methyl, ethyl, propyl, butyl, pentyl or hexyl and their branched isomers.

Preferably, in the catalyst of formula (III), Y is an alkyl ammonium of which the alkyl comprises 1 to 6 carbon atoms chosen from among methyl, ethyl, propyl, butyl, pentyl or hexyl and their branched isomers.

In this particular embodiment, the catalyst of formula (III) is preferably chosen from among CsF, TMAF (tetramethylammonium fluoride) or TBAF (tetrabutylammonium fluoride).

According to a particular embodiment of the invention, the Lewis base-type catalyst is a fluorosilicate chosen from among:
$SiF_6^{2-}$ hexafluorosilicates with an alkaline counterion chosen from among Li, Na, K and Cs; or
fluorosilicates of formula $(R^7)_3SiF_2^-$ with an alkyl ammonium counterion of formula $N(R^{10})_4^+$ or a sulfonium counterion of formula $S(R^{11})_3^+$; with
$R^7$ being an alkyl comprising 1 to 6 carbon atoms chosen from among methyl, ethyl, propyl, butyl, pentyl or hexyl and their branched isomers; or an aryl comprising 6 to 10 carbon atoms chosen from among phenyl, benzyl or naphthyl;
$R^{10}$ being a hydrogen atom; a methyl, an ethyl, a propyl, a butyl, and their branched isomers.
$R^{11}$ being a hydrogen atom; a methyl, an ethyl, a propyl, a butyl, and their branched isomers or primary, secondary or tertiary amines.

In this particular embodiment, the fluorosilicate is potassium hexafluorosilicate ($K_2SiF_6$), or tetrabutylammonium difluorotriphenylsilicate (n-Bu)$_4N^+$ (Ph)$_3SiF_2^-$ also called TBAT.

According to another particular embodiment of the invention, the Lewis base-type catalyst is a primary or secondary amide or a guanidine derivative chosen from among
bicyclic sodium or potassium guanidinates, in particular sodium or potassium salt of the anion of 1,3,4,6,7,8-hexahydro-2H-pyrimido[1,2-a]pyrimidine (or Hhpp),
guanidine,
1,5,7-triazabicyclo[4.4.0]dec-5-ene (or TBD).

According to another particular embodiment of the invention, the Lewis base-type catalyst can also be a carbenic heterocycle of general formula (IV):

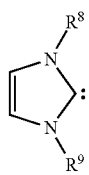  (IV)

wherein
$R^8$ et $R^9$ represent, independently from one another, an alkyl comprising 1 to 6 carbon atoms, an alkenyl comprising 2 to 6 carbon atoms, an alkynyl comprising 2 to 6 carbon atoms or a bi- or tri-cyclic aryl comprising 6 to 20 carbon atoms.

In this embodiment, preferably $R^8$ and $R^9$ independently from one another, is an alkyl comprising 1 to 6 carbon atoms chosen from among methyl, ethyl, propyl, butyl, pentyl or hexyl and their branched isomers; or an aryl comprising 6 to 10 carbon atoms chosen from among phenyl, benzyl, naphthyl.

The carbenic heterocycle can be chosen, for example, from among 2,6-di(1,3-diisopropyl)imidazolium, carbene, 1,3-bis(1-adamantanyl)imidazolium carbene or also 1,3-bis-(2,6-diisopropylphenyl)imidazolinium carbene.

According to another particular embodiment of the invention, the Lewis base-type catalyst can be a carbonate of formula (V)

  (V)

wherein
M' is an alkaline metal chosen from among Li, Na, K, Cs or Rb.

In this embodiment, M' is more specifically Na, K or Cs.

All preferred catalysts, whether they are of formula (II), (III), (IV) or (V), are commercial and not very expensive as indicated below. For example, tBu-OK is a very active and versatile catalyst for reducing oxygenated plastics. Potassium metal is an abundant and inexpensive metal;

TBAT is a catalyst which does not contain metal, can be easily obtained anhydrous and is very active; and TBAF is a very cheap metal-free catalyst. It can be obtained commercially in the form of 1M solution in THF.

Some of the abbreviations used in the context of the invention are represented below:

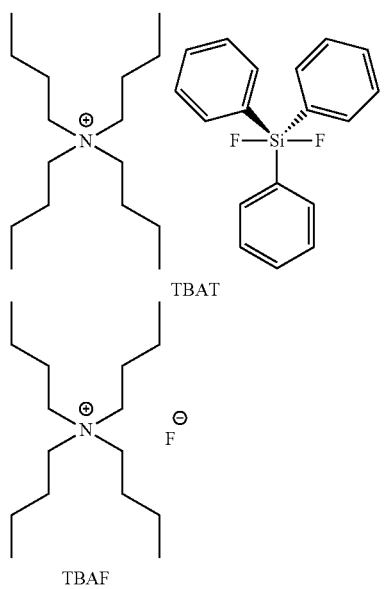

TBAT

TBAF

Catalysts can, if applicable, be immobilised on heterogenic supports in order to ensure an easy separation of said catalyst and/or its recycling. Said heterogenic supports can be chosen from among silica gel- and plastic polymer-based supports like, for example, polystyrene; the carbon supports chosen from among carbon nanotubes; silica carbide; alumina; and magnesium chloride ($MgCl_2$).

According to a particular embodiment of the invention, the depolymerisation method, implements a hydrosilane compound of formula (I) wherein $R^1$, $R^2$ and $R^3$ represent, independently from one another, a hydrogen atom; a hydroxyl group; an alkyl group chosen from among methyl, ethyl, propyl, butyl, and their branched isomers; an alkoxy group of which the alkyl radical is chosen from among methyl, ethyl, propyl, butyl and their branched isomers; an alkoxy group of which the alkyl radical is chosen from among methyl, ethyl, propyl, butyl and their branched isomers; an aryl group chosen from among phenyl and benzyl; an aryloxy group of which the aryl radical is chosen from among phenyl and benzyl; a siloxy group (—O—Si (X')$_3$) of which each X', independently from one another, is chosen from among a hydrogen atom, an alkyl group chosen from among methyl, ethyl, propyl, an aryl group chosen from among phenyl and benzyl, a polymeric organosilane of general formulas

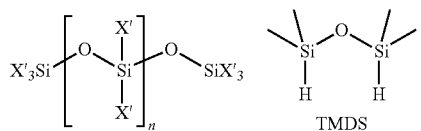

TMDS

-continued

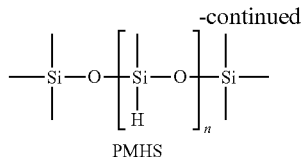

PMHS wherein X' is such as defined above and n is an integer comprised between 1 and 20000, advantageously between 1 and 5000, more advantageously between 1 and 1000; said alkyl, alkoxy, aryl, aryloxy, siloxy and aryl groups being optionally substituted.

In a particular embodiment of the invention, the depolymerisation method, implements a hydrosilane compound of formula (I), wherein $R^1$, $R^2$ and $R^3$ represent, independently from one another, a hydrogen atom; an alkyl group chosen from among methyl, ethyl, propyl and its branched isomer; an aryl group chosen from among benzyl and phenyl; a siloxy group chosen from among polydimethylsiloxane (PDMS), polymethylhydroxysiloxane (PMHS) and tetramethyldisiloxane (TMDS).

PMHS and TMDS which are both by-products of the silicone industry, can be enhanced in the depolymerisation method according to the invention. The use of two industrial by-products to create molecules having a high added value, is economically very advantageous.

As already indicated, the depolymerisation method is carried out under very mild operating conditions: low temperature and pressure, relatively short reaction duration. A total conversion of the starting reagents can be obtained in a few minutes to a few hours. It must be noted that the conversion is expressed with respect to the oxygenated polymer material.

In the method according to the invention, the depolymerisation can be carried out under a pressure of one or of a mixture of inert gas(es) chosen from among nitrogen and argon, or from gases generated by the method in particular of hydrosilane $SiH_4$ and hydrogen. The pressure can be comprised between 0.2 and 5 bars, preferably between 1 and 2 bars, limits included.

The depolymerisation can be carried out at a temperature comprised between 0 and 100° C., preferably between 15 and 75° C., limits included.

The duration of the reaction depends on the conversion rate of the hydrosilane compound of formula (I), on the nature of the hydrosilane of formula (I), as well as the nature of the starting polymer material.

The depolymerisation can be carried out for a duration of 1 minute to 200 hours, advantageously from 1 minute to 48 hours, preferably 10 minutes to 48 hours, limits included.

The depolymerisation, in particular the reaction between the different reagents, ca occur in one or in a mixture of at least two solvent(s) chosen from among:

aromatic hydrocarbons, preferably, chosen from among benzene, toluene, mesitylene;

ethers, preferably chosen from among THF, diethyl ether, Me-THF, anisole.

The depolymerisation, in particular the reaction between the different reagents, can occur in the absence of solvent. In this case, the hydrosilane of formula (I) serves as both reagent and solvent.

The use of TMDS can be mentioned, as well as the use of trimethoxysilane or also triethoxysilane as hydrosilane serving as reagents and solvents for the depolymerisation of the PLA or of the PET.

The hydrosilanes of formula (I) and the catalysts used in the depolymerisation step are, generally, commercial compounds, or compounds which can be prepared by methods known to a person skilled in the art.

The molar ratio between the hydrosilane compound of formula (I) and the oxygenated polymer can be comprised between 0.1 and 20, preferably between 0.5 and 10, limits included.

The quantity of catalyst used in the depolymerisation method can be from 0.001 to 1 molar equivalent, preferably from 0.001 to 0.9 molar equivalent, more preferably from 0.01 to 0.7 molar equivalent, even more preferably from 0.01 to 0.5 molar equivalent, limits included, with respect to the initial number of moles of the starting oxygenated polymer.

After the depolymerisation, the resulting compounds are in silylated form. A simple hydrolysis under conditions well-known to a person skilled in the art can then lead to corresponding saturated or unsaturated aromatic or non-aromatic (aliphatic) compounds in their non-silylated forms.

In the context of the present invention, by hydrolysis, it is meant a method for transforming silylated compounds coming from depolymerisation of the oxygenated polymer, into hydroxyl groups, by a desilylation reaction. This transformation can be achieved under acid or basic conditions or in the presence of fluoride ions, these conditions being well-known to a person skilled in the art. In the context of the present invention, the hydrolysis method is, preferably, chosen from among: HCl or $H_2SO_4$ 2 M in THF; NaOH or KOH 10% in a water/THF mixture; NaOH or KOH 10% in methanol; $TBAF.3H_2O$ in THF; commercial TBAF (1M) solution in THF.

One single filtration can allow to recover the catalyst optionally supported and to eliminate the possible by-products.

The compounds coming from the depolymerisation are obtained with a good purity, i.e. a purity greater than or equal to 90 mol %, preferably comprised between 90 and 99.9 mol %. The molar purity can be determined by a spectroscopic or chromatographic analysis, for example the NMR of the proton ($^1H$ NMR) or the chromatography in the gaseous phase coupled with the mass spectroscopy (GC-MS). Indeed, in the method of the invention, the compounds formed can be easily purified by separation techniques, well-known to a person skilled in the art and conventionally used in this field, like for example, column chromatography, distillation for volatile products, etc. The compounds obtained being generally small molecules, i.e. molecules having a molar mass less than 600 g/mol, their separation of secondary products possibly formed which are generally oligomers with bonds which could not be cleaved by the method of the invention, is easy, given the physico-chemical properties, very different from said oligomers and from the compounds obtained.

The method of the invention is of a great robustness, as it is resistant to the contaminants possibly present in commercial polymer materials (like water traces and metal traces), as well as additives like colourants, added to polymer materials, like for example, plastics.

The method of the invention can be used for recycling composite materials, like resins containing PVC and PET, and which are problematic to recycle. Indeed, the ester bonds of the PET are cleaved, while the C—C bonds of the PVC remain intact.

This method can provide a solution for storing waste by allowing the recycling of the mixture of waste such as PET and PLA. Indeed, given their resemblance to the level of physical and visual properties, plastics (PET) and bioplastics (PLA) are commonly mixed. However, their separation is very expensive and current recycling methods do not allow to recycle the two polymers at the same time. There is therefore a real problem of recycling mixtures of plastics (PET) and of bioplastics (PLA). The method of the invention allows to recycle a mixture of PET and of PLA, either by cleaving the PET selectively, or by cutting the PET and the PLA and this according to the operating conditions chosen.

Thus, object of the invention is to use the depolymerisation method of the invention to recycle plastic materials containing at least one oxygenated polymer in the sense of the invention. In particular, the object of the invention is to use the method of the invention to recycle plastics or mixtures of plastics containing at least one oxygenated polymer, i.e. a polymer or copolymer of which the main chain comprises ester functions and/or carbonates, like for example, PLA, PET, PC-BPA, etc.

The invention also relates to a method for recycling plastic materials or mixtures of plastic materials containing at least one oxygenated polymer in the sense of the invention, i.e. a polymer or copolymer of which the main chain comprises ester functions and/or carbonates, like for example PLA, PET, PC-BPA, comprising (i) a step of depolymerising oxygenated polymer materials according to the invention, optionally (ii) a step of hydrolysis and optionally (iii) a step of functionalisation and/or defunctionalisation. The defunctionalisation here means the reduction of alcohol in alkane i.e. "replacing" the oxygen of the molecule with a hydrogen.

At the end of the depolymerisation method of the invention and after hydrolysis, mono- or polyoxygenated aromatic or saturated or unsaturated non-aromatic (or aliphatic) compounds, like for example, di- and/or tri-oxygenated, of molecular weight less than 600 g/mol, like for example, substituted coniferols, phenol, aromatic polyols, quinines, derivatives of catechols and of hydroxycatechol can be obtained when the starting oxygenated polymer contains aromatic units. The α-ω diols such as ethylene glycol, diethylene glycol, 1,6-hexanediol, 1,4-butanediol, as well as methanol, propylene glycol can, for example, be obtained when the polymers contain saturated or unsaturated aliphatic units. These compounds can be used as fuel, synthetic intermediates, raw materials in the construction sectors, in the petrochemical industry, in the electrical industry, in the electronics industry, in the textile industry, in the aeronautics industry, in the pharmaceutical industry, in the cosmetics industry, in the agrochemical industry.

The object of the invention is therefore a method for preparing mono-, di-, and/or tri-cyclic aromatic compounds, of which each cycle can optionally be mono-, or polyoxygenated, like for example, di- and/or tri-oxygenated comprising (i) a step of depolymerising oxygenated polymers according to the method of the invention, optionally (ii) a step of hydrolysis to form the corresponding non-silylated compounds, optionally (iii) a step of functionalisation and/or defunctionalisation, to obtain other compounds of high added values.

In the context of the present invention, the term "functionalisation" means the replacement of oxygen by another function. In this regard, for example, the substitution of oxygens with halogens can be mentioned (i.e. chlorine, bromine, iodine), azides, amines, or the oxidation of alcohols or the acylation or the dehydration of oxygens.

In the context of the present invention, the term "defunctionalisation" means the replacement of oxygen with a hydrogen, optionally going through a step of functionalisation as defined above.

The object of the invention is also a method for preparing saturated or unsaturated mono-, or polyoxygenated, non-aromatic (or aliphatic) compounds, like for example, di- and/or tri-oxygenated comprising (i) a step of depolymerising oxygenated polymers according to the method of the invention, optionally (ii) a step of hydrolysis to form corresponding non-silylated compounds and optionally (iii) a step of functionalisation and/or defunctionalisation.

The non-aromatic (or aliphatic) compounds saturated or unsaturated mono-, or polyoxygenated, like for example, di- and/or tri-oxygenated and/or of aromatic compounds mono-, di- and/or tri-cyclic of which each cycle can optionally be mono-, or polyoxygenated, like for example, di- and/or tri-oxygenated, obtained by the method for depolymerising oxygenated polymer materials according to the invention, can be used in manufacturing fuels, electronic components, plastic polymers, rubber, medicaments, vitamins, cosmetic products, perfumes, food products, synthetic yarns and fibres, synthetic leathers, glues, pesticides, fertilisers.

Thus, the object of the invention is also a method for manufacturing fuels, electronic components, plastic polymers, rubber, medicaments, vitamins, cosmetic products, perfumes, food products, synthetic yarns and fibres, synthetic leathers, glues, pesticides, fertilisers comprising (i) a step of depolymerising oxygenated polymer materials according to the method of the invention, optionally (ii) a step of hydrolysis to form, for example, the non-aromatic (or aliphatic) compounds saturated or unsaturated mono-, or polyoxygenated, like for example, di- and/or tri-oxygenated and/or aromatic compounds mono-, di-, and/or tri-cyclic of which each cycle can optionally be mono-, or polyoxygenated, like for example, di- and/or tri-oxygenated, and optionally (iii) a step of functionalisation and/or defunctionalisation.

Other advantages and features of the present invention will appear upon reading the examples below, given in an illustrative and non-limiting manner and figures appended, wherein:

FIG. 1 represents the reduction of oxygenated polymers with Lewis acid catalysts that are BCF ($B(C_6F_5)_3$) and the iridium complex according to Cantat et al (WO2016/098021, Feghali et al. *Chem Sus Chem*, 2015, 8, 980-984 et Monsigny et al. *ACS Sustainable Chem. Eng.*, 2018, 6, 10481-10488).

FIG. 2 represents the use of Lewis acid-type catalyst to reduce biomass. (a) The reduction of cellulose with the $B(C_6F_5)_3$ catalyst (Gagné et al., *Angew. Chem. Int. Ed.* 2014, 53, 1646-1649) and (b) the reduction of lignin with the $B(C_6F_5)_3$ and [Ir] catalysts according to Cantat. (Cantat et al. WO2016005836Al, Feghali et al. *Energy Environ. Sci.*, 2015, 8, 2734-2743, Monsigny et al. *Green Chem.*, 2018, 20, 1981-1986).

FIG. 3 represents the reduction of aryl ether bonds in lignin models (i.e. oxygen carbon bond between two aromatics in a molecule mimicking a bond present in a lignin polymer) with potassium terbutanolate (KOtBu) non-catalytically (2-3 equivalents) (Gruber et al., Chem. Sci., 2013, 4, 1640).

Figure 4:
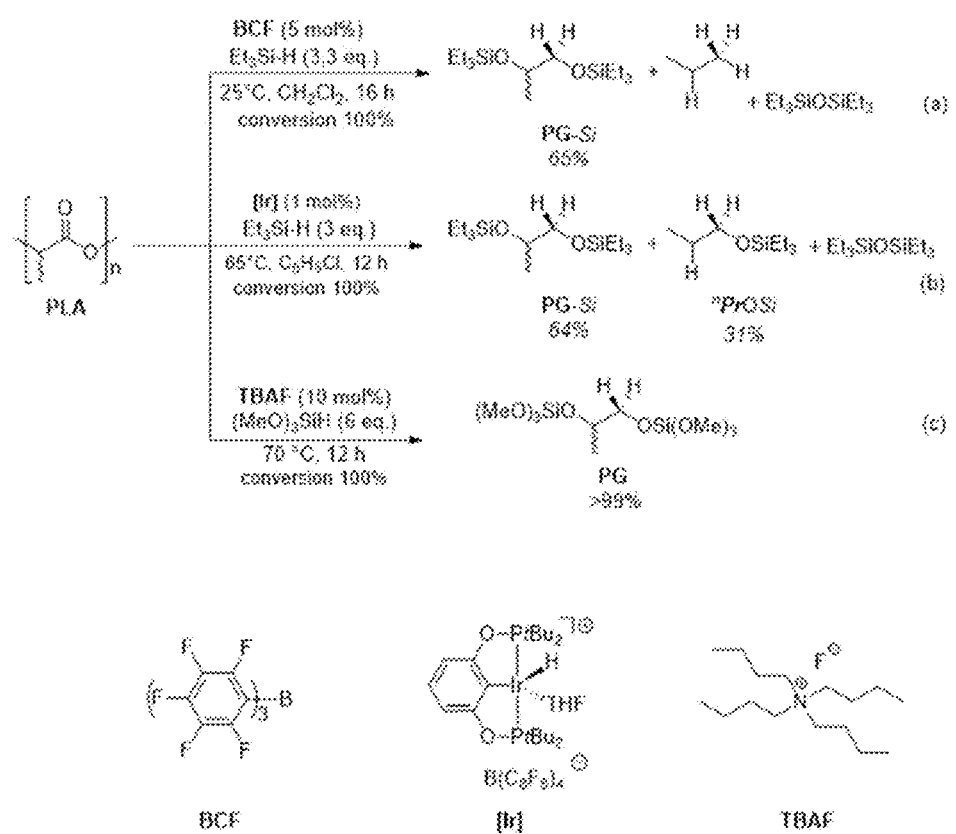

FIG. 4 is a schematic representation comparing the depolymerisation of PLA by the depolymerisation method of the invention (c) with the methods of the state of the art (Cantat et al. WO2016/098021 and *Chem Sus Chem*, 2015, 8, 980-984 (a); Monsigny et al. *ACS Sustainable Chem. Eng.*, 2018, 6, 10481-10488 (b)).

(a) Cantat et al. WO2016/098021, the mixture of triethylsilane ($Et_3SiH$, 3.3 equivalents) and PLA (1 equivalent) in the presence of BCF (5 mol %), as catalyst leads to the production of silyl alcohol corresponding to the monomers of the PLA (PG-Si for silylated propylene glycol), but also to a significant quantity of propane.

(b) Monsigny et al. *ACS Sustainable Chem. Eng.*, 2018, 6, 10481-10488, under similar conditions with an iridium-based catalyst [Ir] leads to a mixture of products: PG-Si is still the main compound, but unlike the reaction with BCF, the main by-product is silylated propanol and not propane.

(c) Finally, in the method of the invention, the use of TBAF which is a Lewis base, as catalyst, does not allow the cleavage of simple bonds σ-C—O such as alcohols and ethers. The depolymerisation reaction of the PLA in the presence of trimethoxysilane which here also serves as solvent leads to the quantitative formation of the sole product PG-Si.

EXAMPLES

In the examples below, only the most commonly used polymers (for example, PCL, PET, PC-BPA and PLA) have been tested. On the other hand, the quantity of hydrosilane of general formula (I) necessary to realize the depolymerisation is largely dependent on the type of polymeric material used to obtain silylated alcohols ($—OSiR^1R^2R^3$). It must be noted that, by approximation, and in order to calculate the molar yield of depolymerisation reactions, the starting material is considered to be exclusively formed from the polymer studied.

The yields obtained are of the order of 68 to 99 mol % with respect to the mole number of monomer in the starting polymer. The conversions have been calculated by being based on spectroscopic analyses ($^1H$ NMR and $^{13}C$ NMR) by using a Bruker DPX 200 MHz spectrometer, and by adding an internal standard (mesitylene or diphenylmethane). The yields have been obtained using gaseous phase chromatography by using as standard, the same compound previously synthesised (external calibration curve). The mass spectrometry data have been collected on a Shimadzu GCMS-QP2010 Ultra gas chromatograph mass spectrometer device equipped with a Supelco SLB™-ms molten silica capillary column (30 m×0.25 mm×0.25 μm). The qualitative analyses of gas have been carried out using gaseous phase chromatography on a Shimadzu GC-2010 device equipped with a Carboxen™ 1006 PLOT capillary column (30 m×0.53 mm).

General Experimental Depolymerisation Protocol

1. Under argon or nitrogen inert atmosphere, the hydrosilane of general formula (I), the oxygenated polymer and the solvent (if necessary) are stirred in a Schlenk tube. The hydrosilane concentration in the reactional mixture varies from 1.0-6.0 mol·$L^{-1}$ (concentration calculated based on half of the final volume of solvent introduced).

2. Then, the catalyst is added to the reactional mixture (1 to 0.001 molar equivalents calculated with respect to the number of moles of polymer material initially added). The solution is stirred and the Schlenk tube is left open in order to discharge the gases produced by the reaction.

3. After the end of adding the solution and stopping the gaseous emission, the Schlenk tube is closed and is left to stir. In the case where the starting material is insoluble, the solubilisation is carried out during the reaction time, given the end products are soluble in the solvents used. The following reaction is carried out by $^1$H NMR and by GC-MS.
4. Once the reaction has ended (reaction time of 1 minute to 24 hours), the solvent, as well as the volatile compounds are evaporated using a Schlenk line ($10^{-2}$ mbar). The oil obtained is purified using a silica gel chromatography by using an elution gradient of 100:0% up to 0:100% of pentane:$CH_2Cl_2$.
5. The products can be hydrolysed by using NaOH (10%) in methanol, to provide the corresponding hydrolysed product. The hydrolysis reaction lasts from 1 minute to 16 hours. The end product is obtained after purification on chromatographic column by using an elution gradient of 100:0% up to 0:100% of $CH_2Cl_2$:AcOEt.

A set of results is presented below, giving examples of depolymerising synthetic and semi-synthetic oxygenated polymer materials.

The catalysts tested are TBAT, TBAF and KOtBu.

The hydrosilanes used are $PhSiH_3$, $(MeO)_3SiH$, $(EtO)_3SiH$ TMDS and PMHS. The oxygenated polymer materials used are PLA, PC-BPA, PCL, PET and PDO. The PET used is a commercial PET sampled from Evian bottles.

Example 1: Depolymerisation of PC-BPA with trimethoxysilane ($(MeO)_3SiH$) with KOtBu

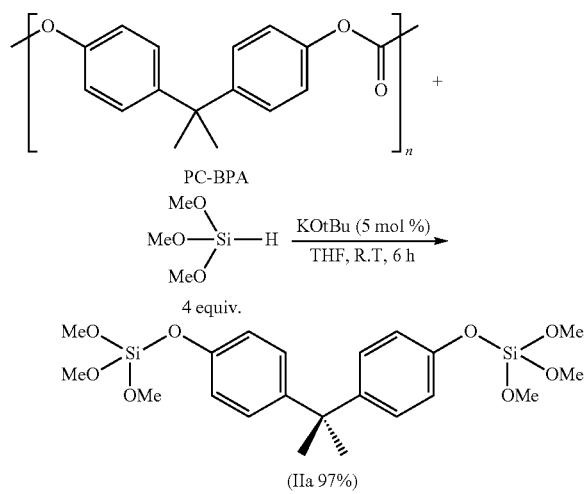

Commercial PC-BPA (123.2 mg; 0.5 mmol; 1 molar equivalent) and trimethoxysilane (244 mg; 2 mmol; 4 molar equivalent) have been added to 1.5 mL of THF. The KOtBu catalyst (0.05 molar equivalent) is added while stirring. After 6 hours of room temperature reaction (20±5° C.), the solvent is evaporated under vacuum. The product obtained IIa is purified by using the same conditions as that described in the general operating method. Coming from this purification, the product IIa is obtained with a very high purity with a yield of 97% with respect to the starting material introduced.

The hydrolysis of the product IIa in corresponding dehydroxylated product can be carried out directly by adding to the reactional mixture, 10 ml of a NaOH solution (10%) in a methanol/water mixture by adding it at 25° C. for 2 hours. The hydrolysed product (BPA) is obtained with a yield of 88%, as white solid, after purification on chromatographic column, by using the conditions described in the general operating method.

Example 2: depolymerisation of PC-BPA with trimethoxysilane ($(MeO)_3SiH$) with TBAT

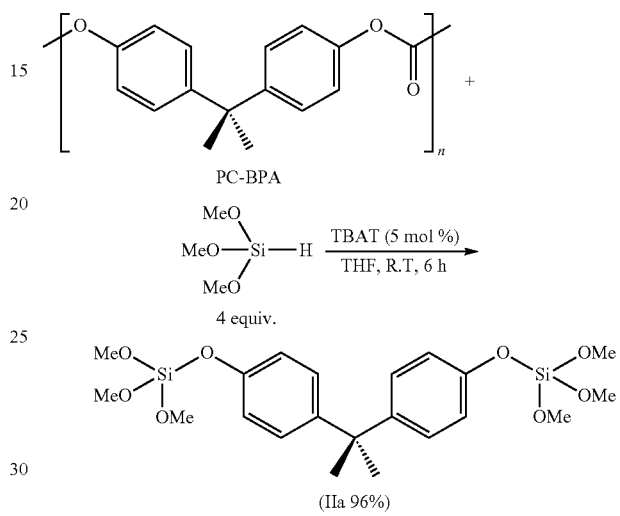

The same operating method used for the depolymerisation of PC-BPA by $(MeO)_3SiH$ with KOtBu in example 1 is used for the depolymerisation with TBAT (0.05 molar equivalent). In this case, 123.2 mg of PC-BPA (0.5 mmol; 1 molar equivalent) are used with 244 mg of trimethoxysilane (244 mg; 2 mmol; 4 molar equivalent) and 0.05 molar equivalent of TBAT (13.5 mg, 0.025 mmol, 5 mol %). After 6 hours of reaction, the conversion is total in IIa. The purification of the products is carried out by following the same operating method described in example 1.

The hydrolysis of the product IIa leads to the obtaining of BPA (white solid, 92% yield).

Example 3: Depolymerisation of PC-BPA with Trimethoxysilane ($(MeO)_3SiH$) with TBAF (1M in THF)

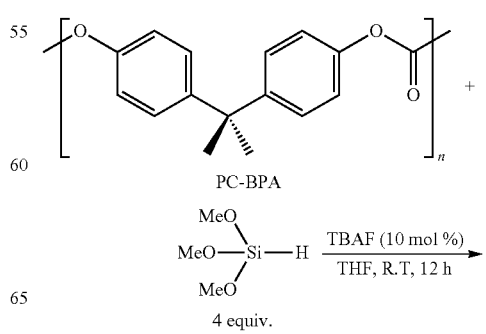

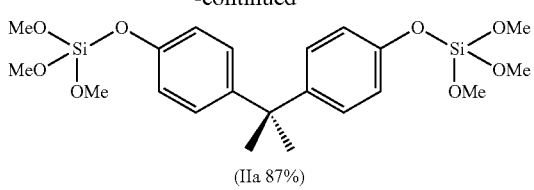

(IIa 87%)

The same operating method used for the depolymerisation of PC-BPA by (MeO)₃SiH with KOtBu in example 1 is used for the depolymerisation with TBAF (1M in THF). In this case, 123.2 mg of PC-BPA (0.5 mmol; 1 molar equivalent) are used with trimethoxysilane (244 mg; 2 mmol; 4 molar equivalent) and 50 of TBAF (0.05 mmol; 0.1 molar equivalent). After 12 hours of reaction, the conversion is total in IIa.

The purification of the products is carried out by following the same operating method described in example 1. The hydrolysis of the product IIa leads to the obtaining of BPA (white solid, 92% yield).

Example 4: depolymerisation of PC-BPA with triethoxysilane ((Et₀)₃SiH) with TBAF (1M in THF)

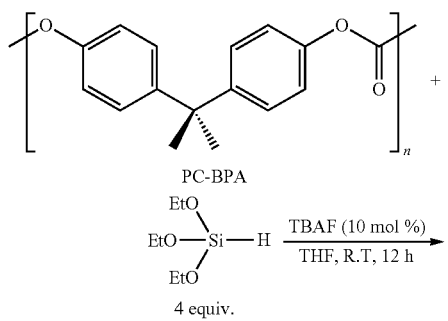

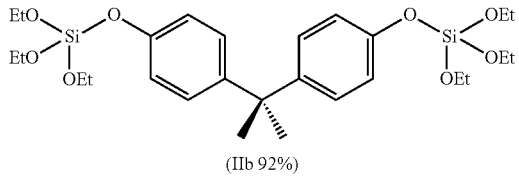

(IIb 92%)

The same operating method used for the depolymerisation of PC-BPA by (MeO)₃SiH with TBAF in example 3 is used for the depolymerisation with triethoxysilane. In this case, 123.2 mg of PC-BPA (0.5 mmol; 1 molar equivalent) are used with 4 molar equivalent of triethoxysilane (328 mg; 2 mmol); and 50 of TBAF (0.05 mmol; 0.1 molar equivalent). After 12 hours of reaction, the conversion is total in IIa. The purification of the products is carried out by following the same operating method described in example 1.

The hydrolysis of the product IIb leads to the obtaining of BPA (white solid, 92% yield).

Example 5: Depolymerisation of PC-BPA with TMDS with TBAF (1M in THF)

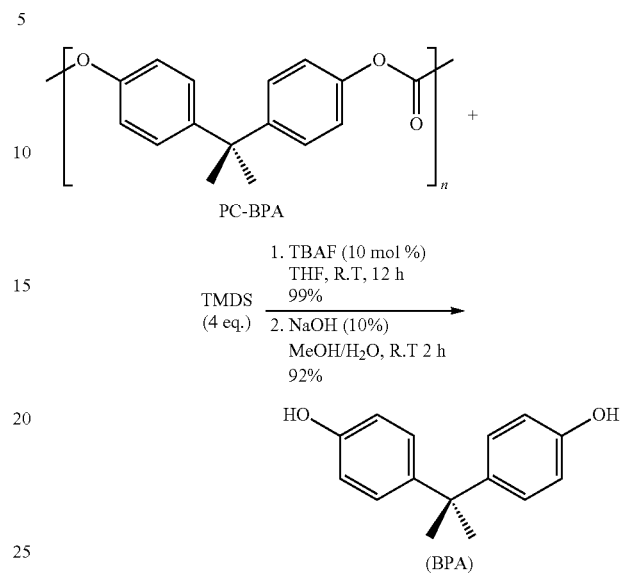

The same operating method used for the depolymerisation of PC-BPA by (MeO)₃SiH with TBAF in example 3 is used for the depolymerisation with TMDS. In this case, 123.2 mg of PC-BPA (0.5 mmol; 1 molar equivalent) are used with (266.7 mg; 2.0 mmol; 4 molar equivalent) of TMDS and (50; 0.05 mmol; 0.1 molar equivalent) of TBAF 0.1 molar equivalent. After 12 hours of reaction, the conversion is total in silylated monomer.

The hydrolysis of silylated monomers is therefore done directly in the reactional medium and leads to the obtaining of BPA (white solid, 92% yield).

Example 6: Depolymerisation of PC-BPA with PMHS with TBAF (1M in THF)

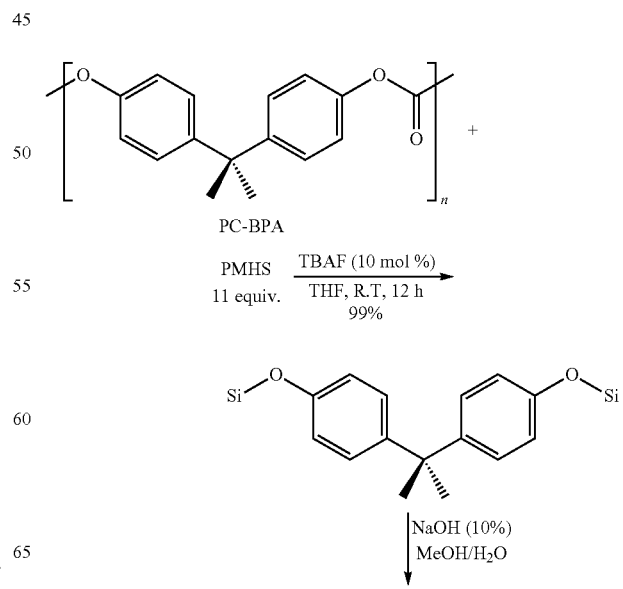

-continued

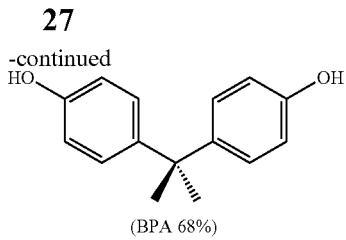

(BPA 68%)

The same operating method used for the depolymerisation of PC-BPA by (MeO)₃SiH with TBAF in example 3 is used for the depolymerisation with PMHS. In this case, 123.2 mg of PC-BPA (0.5 mmol; 1 molar equivalent) are used with 330.7 mg of PMHS (5.5 mmol; 11 molar equivalent) and 504 of TBAF (0.05 mmol; 0.1 molar equivalent).

After 12 hours, the hydrolysis of silylated monomers is done directly in the reactional medium and leads to the obtaining of BPA (white solid, 68% yield).

Example 7: Depolymerisation of PET by Using TMDS with TBAF (1M in THF)

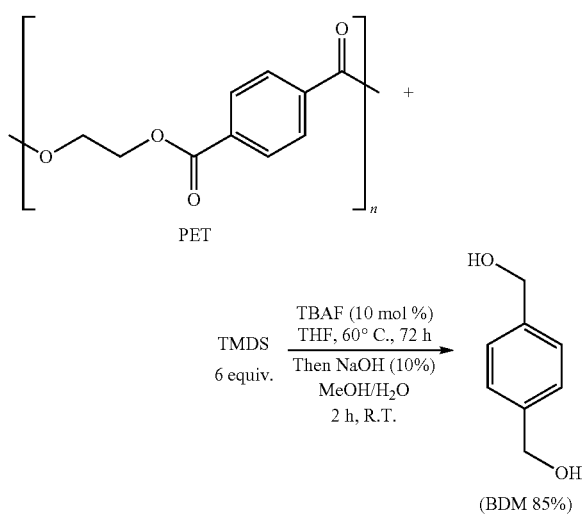

(BDM 85%)

The same operating method used for the depolymerisation of PC-BPA by (MeO)₃SiH with TBAF in example 3 is used for the depolymerisation with PMHS. In this case, 96.1 mg of PET (0.5 mmol; 1 molar equivalent) are used with TMDS (400.0 mg; 3.0 mmol; 6 molar equivalent) and 0.1 molar equivalent of TBAF (50 µL; 0.05 mmol; 0.1 molar equivalent). After 72 hours at 60° C., the hydrolysis of the silylated product is done directly in the reactional medium and leads to the obtaining of BDM (white solid, 85% yield).

Example 8: Depolymerisation of PCL by Using TMDS with TBAF (1M in THF)

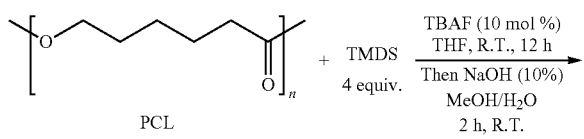

-continued

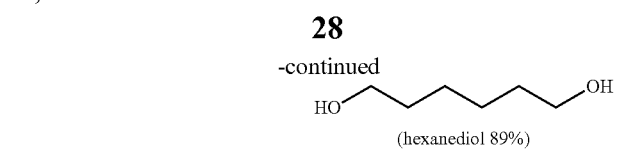

(hexanediol 89%)

The same operating method used for the depolymerisation of PC-BPA by (MeO)₃SiH with TBAF in example 3 is used for the depolymerisation with PMHS. In this case, (58.2 mg; 0.5 mmol; 1 molar equivalent) of PCL are used with 266.7 mg of TMDS (2.0 mmol; 4 molar equivalent) and 504 of TBAF (0.05 mmol; 0.1 molar equivalent). After 12 hours at room temperature (20±5° C.), the hydrolysis of the silylated product is done directly in the reactional medium and leads to the obtaining of 1,6-hexanediol (white solid, 89% yield).

Example 9: Depolymerisation of PLA by Using TMDS with TBAF (1M in THF)

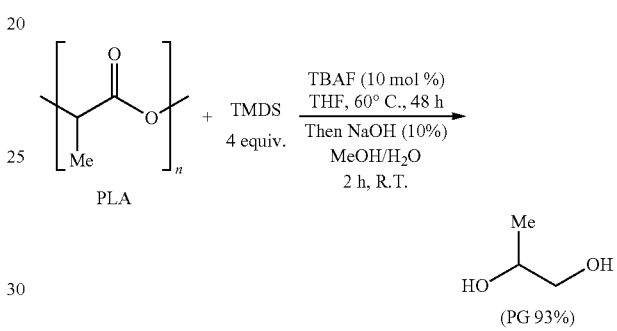

(PG 93%)

The same operating method used for the depolymerisation of PC-BPA by (MeO)₃SiH with TBAF in example 3 is used for the depolymerisation with PMHS. In this case, (37.0 mg; 0.5 mmol; 1 molar equivalent) of PLA are used with 266.7 mg of TMDS (2.0 mmol; 4 molar equivalent) and 504 of TBAF (0.05 mmol; 0.1 molar equivalent). After 48 hours at 60° C., the hydrolysis of the silylated product is done directly in the reactional medium and leads to the obtaining of propylene glycol (white oil, 93% yield).

Example 10: Depolymerisation of PDO by Using TMDS with TBAF (1M in THF)

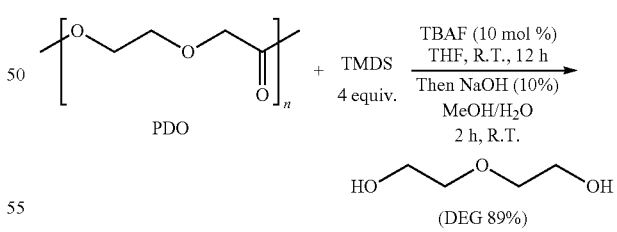

(DEG 89%)

The same operating method used for the depolymerisation of PC-BPA by (MeO)₃SiH with TBAF in example 3 is used for the depolymerisation with PMHS. In this case, 52.2 mg of PDO (0.5 mmol; 1 molar equivalent) are used with 266.7 mg of TMDS (2.0 mmol; 4 molar equivalent) and 504 of TBAF (0.05 mmol; 0.1 molar equivalent). After 12 hours at room temperature (20±5° C.), the hydrolysis of the silylated diethyleneglycol is done directly in the reactional medium and leads to the obtaining of diethyleneglycol DEG (colourless oil, 89% yield).

Example 11

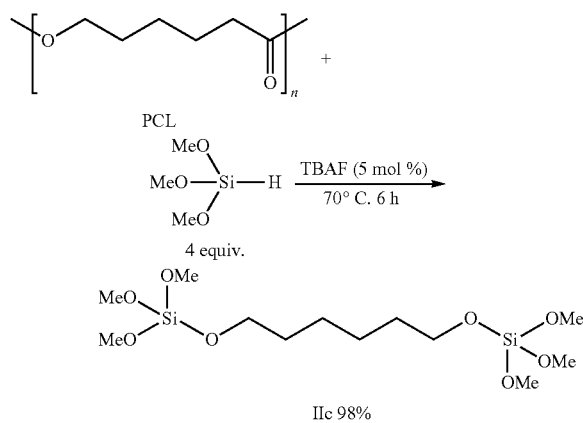

The same operating method used for the depolymerisation of PC-BPA by (MeO)₃SiH with TBAF in example 3 is used for the depolymerisation with PCL with (MeO)₃SiH. In this case, (52.2 mg; 0.5 mmol; 1 molar equivalent) of PCL are used with (244 mg; 2 mmol; 4 molar equivalent) of (MeO)₃SiH and 2.8 mg; (0.025 mmol; 5 mol %) of TBAF without solvent. After 6 hours at 70° C., the purification of the silylated product is carried out by following the same operating method described in example 1 and is obtained at 98%.

Characterisation of the Molecules Obtained:

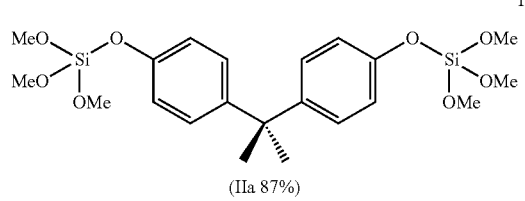

$^1$H NMR (200 MHz, THF-d$_8$, Me$_4$Si) δ (ppm)=7.10 (4H, m, Ar—H̲), 6.86 (4H, m, Ar—H), 3.58 (18H, s, MeOSi), 1.61 (6H, s, CH$_3$—)

$^{13}$C NMR (50 MHz, THF-d$_8$, Me$_4$Si): δ (ppm)=151.1, 144.4, 127.5, 118.4, 50.6, 32.7, 30.5.

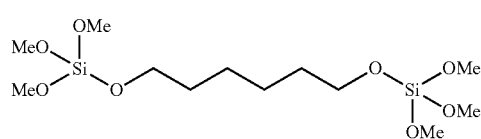

$^1$H NMR (200 MHz, THF-d$_8$, Me$_4$Si) δ (ppm)=3.73 (4H, t$^3$J=6 Hz, O—CH̲$_2$), 1.55 (4H, m, O—CH$_2$—CH̲$_2$—CH$_2$), 1.40 (4H, m, O—CH$_2$—CH$_2$—CH̲$_2$—).

$^{13}$C NMR (50 MHz, THF-d$_8$, Me$_4$Si): δ (ppm)=63.0, 50.2, 32.3, 25.3.

The abbreviations used are specified below:
PC-BPA=Polycarbonate bisphenol A
PCL=Poly(caprolactone)
PDO=Poly(dioxanone)
PET=Poly(ethylene terephthalate)
PVC=Poly(vinyl chloride)
DEG=Diethylene glycol
EG=Ethylene glycol
PG=Propylene glycol
BDM=Benzene dimethanol
TPA=terephthalic acid
PLLA=Poly(L-lactide)
PLA=Polylactic acid
BPA=Bisphenol A
PS=Polystyrene

The invention claimed is:

1. A method for depolymerising oxygenated polymers by selective cleaving of oxygen-carbon bonds of ester functions (—CO—O—) and carbonate functions (—O—CO—O—), wherein the method comprises a step of putting into contact said oxygenated polymers with a hydrosilane compound of formula (I)

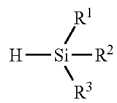

(I)

wherein
$R^1$, $R^2$ and $R^3$ represent, independently from one another, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted, or $R^1$ is a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted, and $R^2$ and $R^3$, taken together with the silicon atom to which they are linked to form an optionally substituted silyl heterocycle;

in presence of a Lewis base catalyst, said Lewis base catalyst being
an alcoholate of formula (II)

$$(R^6-O^-)_w M^{w+} \qquad (II)$$

wherein
w is 1, 2, 3, 4, and 5;
$R^6$ is an alkyl comprising 1 to 6 carbon atoms, an alkenyl comprising 2 to 6 carbon atoms, an alkynyl comprising 2 to 6 carbon atoms or a monocyclic or polycyclic aryl typically bi- or tri-cyclic comprising 6 to 20 carbon atoms; and
M is a metal chosen from among Li, Na, K, Cs or Rb, Cu, Mg, Zn, Ca, Sr, Ba, Pb, Al, Sb, La, Zr, Si, Ti, Sn, Hf, Ge, V; or
a compound allowing to release a fluoride (F⁻) of formula (III):

$$Y^{z+}-(F^-)_z \qquad (III)$$

wherein
z is 1, 2, 3, 4;
Y is an alkyl ammonium of which the alkyl comprises 1 to 6 carbon atoms, an alkenyl ammonium of which the alkenyl comprises 2 to 6 carbon atoms, an alkynyl ammonium of which the alkynyl comprises 2 to 6 carbon atoms, or an aryl comprising 6 to 10 carbon atoms; a quinine ammonium, or Y is a metal chosen from among Li, Na, K, Cs, Rb, Cu, Zn, Ca, Ba, Al, Zr, Sn;

a fluorosilicate chosen from among:

hexafluorosilicates $SiF_6^{2-}$ with an alkaline counterion chosen from among Li, Na, K and Cs; or fluorosilicates of formula $(R^7)_3SiF_2^-$ with an alkyl ammonium counterion of formula $N(R^{10})_4^+$ or a sulfonium counterion of formula $S(R^{11})_3^+$; with

- $R^7$ being an alkyl comprising 1 to 6 carbon atoms chosen from among methyl, ethyl, propyl, butyl, pentyl or hexyl and their branched isomers; or an aryl comprising 6 to 10 carbon atoms chosen from among phenyl, benzyl or naphthyl;
- $R^{10}$ being a hydrogen atom; a methyl, an ethyl, a propyl, a butyl, and their branched isomers;
- $R^{11}$ being a hydrogen atom; a methyl, an ethyl, a propyl, a butyl, and their branched isomers or primary, secondary or tertiary amines;

a primary or secondary amide, a guanidine derivative chosen from among bicyclic sodium or potassium guanidinates, in particular sodium or potassium salt of the anion of 1,3,4,6,7,8-hexahydro-2H-pyrimido[1,2-a]pyrimidine (or Hhpp), guanidine, 1,5,7-triazabicyclo[4.4.0]dec-5-ene (or TBD);

a carbenic heterocycle of general formula (IV):

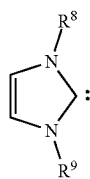

(IV)

wherein $R^8$ and $R^9$ represent, independently from one another, an alkyl comprising 1 to 6 carbon atoms, an alkenyl comprising 2 to 6 carbon atoms, an alkynyl comprising 2 to 6 carbon atoms or a bi- or tri-cyclic aryl comprising 6 to 20 carbon atoms;

a carbonate of formula (V)

(V)

wherein M' is a metal chosen from among Li, Na, K, Cs or Rb.

2. The method according to claim 1, wherein the oxygenated polymers are chosen from among saturated or unsaturated polyesters chosen from among polylactic acid (PLA), polycaprolactone (PCL), polyhydroxyalkanoate (PHA), polyhydroxyvalerate (PHV), polyethylene adipate (PEA), polybutylene succinate (PBS), poly(3-hydroxybutyrate-co-3-hydroxyvalerate (PHBV), polyethylene terephthalate (PET), polybutylene terephthalate (PBT), polytrimethylene terephthalate (PTT), polyethylene naphthalate (PEN), polydioxanone (PDO);

polycarbonates chosen from among PC-BPA, polypropylene carbonate (PPC), polyethylene carbonate (PEC), poly(hexamethylene carbonate), allyl diglycol carbonate (ADC) or CR-39; or hydrolysable tannins chosen from among gallotannins, ellagitannins, or suberin.

3. The method according to claim 1, wherein the oxygenated polymers are chosen from among polyesters chosen from among PET, PCL, PDO or PLA;

polycarbonates chosen from among PC-BPA or PPC;

hydrolysable tannins chosen from among gallotannins, ellagitannins, or suberin.

4. The method according to claim 1, wherein the Lewis base catalyst is an alcoholate of formula (II), wherein $R^6$ is a linear or branched alkyl comprising 1 to 6 carbon atoms, chosen from among methyl, ethyl, propyl, butyl, pentyl or hexyl and their branched isomers and M is Li, Na, K or Rb.

5. The method according to claim 1, wherein the Lewis base catalyst is an alcoholate of formula (II) chosen from among $CH_3$—OLi, $CH_3$—ONa, $CH_3$—OK, $CH_3$—ORb, $CH_3CH_2$—OK, $(CH_3$—$O)_3Al$, $(PhO)_3Al$, $(iPrO)_3Al$ or tBu-OK.

6. The method according to claim 1, wherein the Lewis base catalyst is a compound of formula (III), wherein Y is an alkyl ammonium of which the alkyl comprises 1 to 6 carbon atoms, chosen from among methyl, ethyl, propyl, butyl, pentyl or hexyl and their branched isomers.

7. The method according to claim 1, wherein the Lewis base catalyst is a compound of formula (III), chosen from among CsF, TMAF (tetramethylammonium fluoride) or TBAF (tetrabutylammonium fluoride).

8. The method according to claim 1, wherein the Lewis base catalyst is a fluorosilicate chosen from among fluorosilicate ammonium ($K_2SiF_6$) or difluorotriphenylsilicate tetrabutylammonium $[(n-Bu)_4N^+(Ph)_3SiF_2^-]$ also called TBAT.

9. The method according to claim 1, wherein the Lewis base catalyst is a carbenic heterocycle of formula (IV) chosen from among 2,6-di(1,3-diisopropyl)imidazolium carbene, 1,3-bis(1-adamantanyl)imidazolium carbene or 1,3-bis(2,6-diisopropylphenyl)imidazolinium carbene.

10. The method according to claim 1, wherein the hydrosilane compound implemented is a hydrosilane compound of formula (I) wherein $R^1$, $R^2$ and $R^3$ represent, independently from one another, a hydrogen atom; a hydroxyl group, an alkyl group chosen from among methyl, ethyl, propyl, butyl, and their branched isomers; an alkoxy group of which the alkyl radical is chosen from among methyl, ethyl, propyl, butyl and their branched isomers; an alkoxy group of which the alkyl radical is chosen from among methyl, ethyl, propyl, butyl and their branched isomers; an aryl group chosen from among phenyl and benzyl; an aryloxy group of which the aryl radical is chosen from among phenyl and benzyl; a siloxy group (—O—Si(X')$_3$) of which each X, independently from one another, is chosen from among a hydrogen atom, an alkyl group chosen from among methyl, ethyl, propyl, an aryl group chosen from among phenyl and benzyl, a polymeric organosilane of general formulas

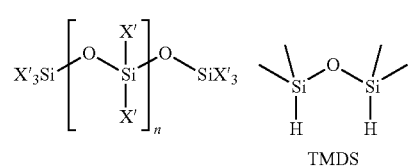

TMDS

-continued

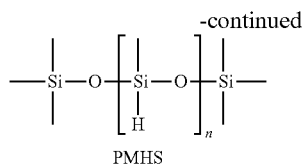
PMHS wherein X' is independently from one another, is chosen from among a hydrogen atom, an alkyl group chosen from among methyl, ethyl, propyl, an aryl group chosen from among phenyl and benzyl, and n is an integer comprised between 1 and 20000, advantageously between 1 and 5000, more advantageously between 1 and 1000; said alkyl, alkoxy, aryl, aryloxy, siloxy and aryl groups being optionally substituted.

11. The method according to claim 1, wherein the hydrosilane compound implemented is a hydrosilane compound of formula (I), wherein $R^1$, $R^2$ and $R^3$ represent, independently from one another, a hydrogen atom; an alkyl group chosen from among methyl, ethyl, propyl and its branched isomer; an aryl group chosen from among benzyl and phenyl; a siloxy group chosen from among polydimethylsiloxane (PDMS), polymethylhydroxysiloxane (PMHS) and tetramethyldisiloxane (TMDS).

12. The method according to claim 1, wherein the molar ratio between the hydrosilane compound of formula (I) and the oxygenated polymer is comprised between 0.1 and 20.

13. He method according to claim 1, wherein the catalyst quantity is from 0.001 to 0.9 molar equivalent, with respect to the initial molar number of the starting oxygenated polymer.

14. A method for recycling plastic materials or mixtures of plastic materials containing at least one oxygenated polymer wherein the method comprises (i) a step of depolymerising oxygenated polymer materials according to claim 1, optionally (ii) a step of hydrolysis and optionally (iii) a step of functionalization and/or defunctionalization.

15. A method for preparing non-aromatic (or aliphatic) compounds, saturated or unsaturated, mono-, di- and/or tri-oxygenated, or mono-, di-, and/or tri-cyclic aromatic compounds, of which each cycle is optionally mono-, di-, and/or tri-oxygenated, wherein the method comprises (i) a step of depolymerising oxygenated polymer materials according to claim 1, optionally (ii) a step of hydrolysis to form the corresponding non-silyl compounds and optionally (iii) a step of functionalisation and/or defunctionalisation.

16. A method for manufacturing fuels, electronic components, plastic polymers, rubber, medicaments, vitamins, cosmetic products, perfumes, food products, yarns and synthetic fibres, synthetic leathers, glues, pesticides, fertilisers, comprising (i) a step of depolymerising oxygenated polymer materials according to claim 1, and optionally (ii) a step of hydrolysis to form the non-aromatic (or aliphatic) compounds, saturated or unsaturated, mono-, di- and/or tri-oxygenated and/or mono-, di-, and/or tri-cyclic aromatic compounds, of which each cycle is mono-, di- and/or tri-oxygenated, optionally (iii) a step of functionalization and/or defunctionalization.

* * * * *